(12) United States Patent
Lo

(10) Patent No.: US 11,141,491 B2
(45) Date of Patent: Oct. 12, 2021

(54) PH-SENSITIVE LIPID NANOPARTICLES FOR ENCAPSULATION OF ANTICANCER DRUGS AND MICRORNA AND USE THEREOF

(71) Applicant: National Yang-Ming University, Taipei (TW)

(72) Inventor: Yu-Li Lo, Taipei (TW)

(73) Assignee: National Yang Ming Chiao Tung University, Taipei (TW)

( * ) Notice: Subject to any disclaimer, the term of this patent is extended or adjusted under 35 U.S.C. 154(b) by 0 days.

(21) Appl. No.: 16/653,322

(22) Filed: Oct. 15, 2019

(65) Prior Publication Data
US 2020/0114019 A1 Apr. 16, 2020

Related U.S. Application Data

(60) Provisional application No. 62/745,600, filed on Oct. 15, 2018.

(51) Int. Cl.
| | |
|---|---|
| *A61K 48/00* | (2006.01) |
| *C07H 21/04* | (2006.01) |
| *A61K 47/69* | (2017.01) |
| *A61K 9/127* | (2006.01) |
| *A61K 31/4745* | (2006.01) |
| *A61K 47/62* | (2017.01) |
| *A61P 35/00* | (2006.01) |
| *C12N 15/113* | (2010.01) |

(52) U.S. Cl.
CPC .......... *A61K 47/6929* (2017.08); *A61K 9/127* (2013.01); *A61K 31/4745* (2013.01); *A61K 47/62* (2017.08); *A61P 35/00* (2018.01); *C12N 15/113* (2013.01); *C12N 2310/141* (2013.01)

(58) Field of Classification Search
CPC .. C12N 15/113; C12N 2310/141; A61P 35/00
See application file for complete search history.

(56) References Cited

U.S. PATENT DOCUMENTS

| | | | | |
|---|---|---|---|---|
| 2011/0038941 A1* | 2/2011 | Lee | ........................ | C12N 15/88 424/498 |
| 2011/0305770 A1* | 12/2011 | Zhao | ....................... | A61P 43/00 424/499 |
| 2015/0017228 A1* | 1/2015 | Hamidi | ................ | A61K 9/5138 424/450 |
| 2015/0265716 A1* | 9/2015 | Valencia | .............. | A61K 31/555 424/490 |
| 2016/0244452 A1* | 8/2016 | Castro | .................. | C07D 487/04 |

FOREIGN PATENT DOCUMENTS

| | | | | | |
|---|---|---|---|---|---|
| JP | 2012050390 A | * | 3/2012 | ........... | C12N 15/113 |
| WO | WO 00/48464 | * | 2/2000 | ........... | A61K 31/713 |
| WO | WO 2011/057003 A2 | * | 5/2011 | ........... | C12N 15/113 |
| WO | WO 2018/234586 A1 | * | 12/2018 | ........... | C12N 15/115 |

OTHER PUBLICATIONS

Scarpati et al. (BioMed Research International, 2014, pp. 1-8).*
Hong et al. (Expert Opin. Ther. Targets, 2013, 17(9), 1073-1080).*
Mansoori et al. (Adv Pharm Bull, 2017, 7(3), 339-348).*

\* cited by examiner

*Primary Examiner* — Amy H Bowman
(74) *Attorney, Agent, or Firm* — Muncy, Geissler, Olds & Lowe, P.C.

(57) ABSTRACT

Currently, the present invention provides a pH-sensitive lipid nanoparticle, comprising: a nanoparticle core composed of a mixture of lipid and/or surfactant, and the surface of the nanoparticle core comprising: a imine-omPEG, the imine is a pH-sensitive linker; and a PEG-peptide, wherein the peptide is selected from the group consisting of a RF peptide, a K peptide, and a H peptide; wherein the RF peptide is a potent CPP, the K peptide is a mitochondria-targeting peptide and the H peptide is a cancer specific binding peptide; a lipid, inside the nanoparticle core; wherein the lipid nanoparticle encapsulating a targeting agent.

14 Claims, 27 Drawing Sheets

Specification includes a Sequence Listing.

PH-SENSITIVE LIPID NANOPARTICLES FOR ENCAPSULATION OF ANTICANCER DRUGS AND MICRORNA AND USE THEREOF

CROSS-REFERENCE TO RELATED APPLICATIONS

This Non-provisional application claims priority under 35 U.S.C. § 119(a) on Patent Application No. 62/745,600 filed in American United States Oct. 15, 2018, the entire contents of which are hereby incorporated by reference.

FIELD OF THE INVENTION

The present invention relates to the pH-sensitive lipid nanoparticles for encapsulation of anticancer drugs and microRNA and use thereof.

BACKGROUND OF THE INVENTION

Colorectal cancer (CRC) begins when healthy cells in the lining of the colon or rectum change and grow out of control, forming a mass called a tumor. Treatments used for colorectal cancer may include some combination of surgery, radiation therapy, chemotherapy and targeted therapy. Cancers that are confined within the wall of the colon may be curable with surgery, while cancer that has spread widely is usually not curable. The five-year survival rate in the United States is around 65%. Globally, colorectal cancer is the third most common type of cancer, making up about 10% of all cases. In 2012, there were 1.4 million new cases and 694,000 deaths from the disease. It is more common in developed countries, where more than 65% of cases are found.

Head and neck cancer is a group of cancers that starts in the mouth, nose, throat, larynx, sinuses, or salivary glands. In 2015, head and neck cancers globally affected more than 5.5 million people (2.4 million mouth, 1.7 million throat, and 1.4 million larynx cancer), and it has caused over 379,000 deaths (146,000 mouth, 127,400 throat, 105,900 larynx cancer). Together, they are the seventh most-frequent cancer and the ninth most-frequent cause of death from cancer. In the United States, about 1% of people are affected at some point in their life, and males are affected twice as often as females. The usual age at diagnosis is between 55 and 65 years old. The average 5-year survival following diagnosis in the developed world is 42-64%.

Irinotecan (Iri), a water-soluble camptothecin, is one of the first-line therapeutic agents for advanced or metastatic colorectal cancer. Irinotecan functions by avoiding religation of the DNA strand via forming a cleavable drug-DNA-topoisomerase I complex, thus causing lethal double-strand DNA breakage and cell death. However, irinotecan is remarkably effluxed by P-glycoprotein (P-gp) and multidrug resistance (MDR)-associated proteins (MRPs) in tumor cells. Resistance and adverse events, including diarrhea, nausea and vomiting usually occur in later stages of irinotecan therapy. How to reduce drug resistance and reduce side effects of irinotecan is an urgent problem in the industry.

MicroRNAs (miRNAs; miRs) play critical roles in modulating mRNA translation. Upregulation of hsa-miR-200c-3p may suppress epithelial-mesenchymal transition (EMT) and inhibit metastasis through suppression of ZEB1/2, Snail and Slug. Furthermore, miR-200 down regulated ZEB1 and vimentin, and increased cancer cell sensitivity to gemcitabine. But the use of miR-200 alone was not sufficient as a single anticancer agent. Additionally, there are the problems for miR delivery into cells, including rapid degradation in the systemic circulation, fast detection by the immune system, low cellular uptake, and poor endosomal escape.

In addition, the anti-cancer drug-encapsulated nanoparticle on the market is reduced to the target of tumor cells due to PEGylation. And the problems are caused by poor internalization, and the shortcomings of no distinction between normal cells and cancer cells. So, there is a great need for the development of new compounds that are effective therapeutic agents for colorectal cancer and head and neck cancer. The currently available treatment regimens are in large encountered with problems of drug resistance and side effects.

SUMMARY OF THE INVENTION

In view of the above-mentioned problem, the present invention provides a pH-sensitive lipid nanoparticle, wherein the lipid nanoparticle encapsulating a targeting agent.

Irinotecan may penetrate and injure normal tissues, including mucosal membranes and results in unwanted side effects, such as diarrhea and vomiting. MicroRNA also shows the disadvantages of rapid degradation and poor cellular uptake. In view of the above-mentioned problem, the present invention provides a pH-sensitive and tumor-targeting delivery system with good penetration for irinotecan and miR to improve the treatment of advanced CRC and HNC, as indicated in FIG. 3. In the present study, Lip and SLN were successfully modified with cell-penetrating RF peptide, NG2-targeting H peptide and mitochondria-targeting K peptide.

A pH-sensitive lipid nanoparticle, comprising a surface of the nanoparticle core, wherein the surface comprising an imine-omPEG, the imine is a pH-sensitive linker a PEG-RF peptide; wherein the RF peptide is a potent cell-penetrating peptide (CPP) a PEG-K peptide; wherein the K peptide is a mitochondria-targeting peptide a PEG-H peptide; wherein the H peptide is a cancer specific binding peptide; and a targeting agent inside the nanoparticle core; wherein the nanoparticle core is composed of a lipid and a phospholipid.

The pH-sensitive lipid nanoparticle, wherein the lipid is a L-α-phosphatidylcholine (PC), glycerol monostearate (monostearin), glycerol monopalmitate or glycerol monooleate.

The pH-sensitive lipid nanoparticle, wherein the phospholipids is PC, DSPE, DPPE, DOPE, and the cationic lipids is DOTAP, DOTMA, SAINT 2, MC3, or KC2.

The pH-sensitive lipid nanoparticle, wherein the nanoparticle core comprised a surfactant, wherein the surfactant is Poloxamers (Pluronics), Tweens, Spans, Brij, Myrj, cyclodextrin derivative, or chitosan derivative.

The pH-sensitive lipid nanoparticle, wherein the targeting agent is a microRNA or a drug.

The pH-sensitive lipid nanoparticle, wherein the microRNA is selected from the group consisting of hsa-miR-21 inhibitor mimics for has-miR-122-5p, hsa-miR-125b-5p, has-miR-136-5p, has-miR-139-5p, has-miR-200c-3p and has-miR-320a.

The pH-sensitive lipid nanoparticle, wherein the drug is selected from the group consisting of irinotecan, oxaliplatin, doxorubicin, afatinib, and docetaxel.

The pH-sensitive lipid nanoparticle, wherein the lipid nanoparticle can be accumulated in the cancer cell in pH 5-7 environment or tumor microenvironment.

The pH-sensitive lipid nanoparticle, wherein the cancer cell comprising colorectal cancer, head cancer and neck cancer or pancreatic cancer.

The pH-sensitive lipid nanoparticle, wherein the RF peptide is SEQ. NO 1. (SEQ. NO 1 GLKKLARLFHKLLKLGC)

The pH-sensitive lipid nanoparticle, wherein the K peptide is SEQ. NO 2. (SEQ. NO 2 CKLAKLAK)

The pH-sensitive lipid nanoparticle, wherein the H peptide is a nerve/glial antigen 2 (NG2) proteoglycan binding peptides.

The pH-sensitive lipid nanoparticle, wherein the H peptide is a SEQ. NO 3. (SEQ. NO 3 CTAASGVRSMH)

A pharmaceutical composition comprising an effective amount of multiple lipid nanoparticle as the pH-sensitive lipid nanoparticle, comprising a microRNA-loaded pH-responsive nanoparticle, wherein the lipid is a mixture of a monoglyceride, a cationic lipid and a surfactant, and the targeting agent is a microRNA; and a drug-loaded pH-responsive nanoparticle, wherein the lipid is a lipid bilayer and the targeting agent is an anticancer drug.

The pharmaceutical composition of the pH-sensitive lipid nanoparticle, wherein the microRNA is selected from the group consisting of hsa-miR-21 inhibitor mimics for has-miR-122-5p, hsa-miR-125b-5p, has-miR-136-5p, has-miR-139-5p, has-miR-200c-3p and has-miR-320a.

The pharmaceutical composition of the pH-sensitive lipid nanoparticle, wherein the anticancer drug is selected from the group consisting of the irinotecan, oxaliplatin, doxorubicin, afatinib, and docetaxel.

A method for treating cancer in a subject, comprising: administering to said subject an effective amount of multiple lipid nanoparticle as the pH-sensitive lipid nanoparticle, comprising a microRNA-loaded pH-responsive nanoparticle, wherein the lipid is a mixture of a monoglyceride, a cationic lipid, and a surfactant and the targeting agent is a microRNA; and a drug-loaded pH-responsive nanoparticle, wherein the lipid is a lipid bilayer and the targeting agent is an anticancer drug.

The method of the pH-sensitive lipid nanoparticle, wherein the cancer comprising colorectal cancer, head and neck cancer or pancreatic cancer.

The method of the pH-sensitive lipid nanoparticle, wherein the anticancer drug is selected from the group consisting of irinotecan, oxaliplatin, epirubicin, doxorubicin, afatinib, and docetaxel.

BRIEF DESCRIPTION OF THE DRAWINGS

FIG. 8A shows CT26-bearing mice were administered with various formulations once a week for 28 d. IVIS images of the mice in different groups were taken at the treatment end of 28 d. n=5; the relative bioluminescence intensity is displayed in the lower panel. *P<0.05; P<0.01; *P<0.001.

FIG. 8B shows PET/CT images of the representative mice from each group. White circles: tumor; yellow circles: bladder; orange circles: heart. *P<0.05; P<0.01; *P<0.001.

FIG. 8C shows tumor size as a function of time in CT-26 bearing mice. *P<0.05; P<0.01; *P<0.001.

FIG. 8D shows body weight as a function of time in CT-26 bearing mice. *P<0.05; P<0.01; *P<0.001.

DETAILED DESCRIPTION OF THE INVENTION

In order to solve above-mentioned problem, the present invention provides a pH-sensitive lipid nanoparticle, wherein the lipid nanoparticle encapsulating a targeting agent.

Figure 1A:
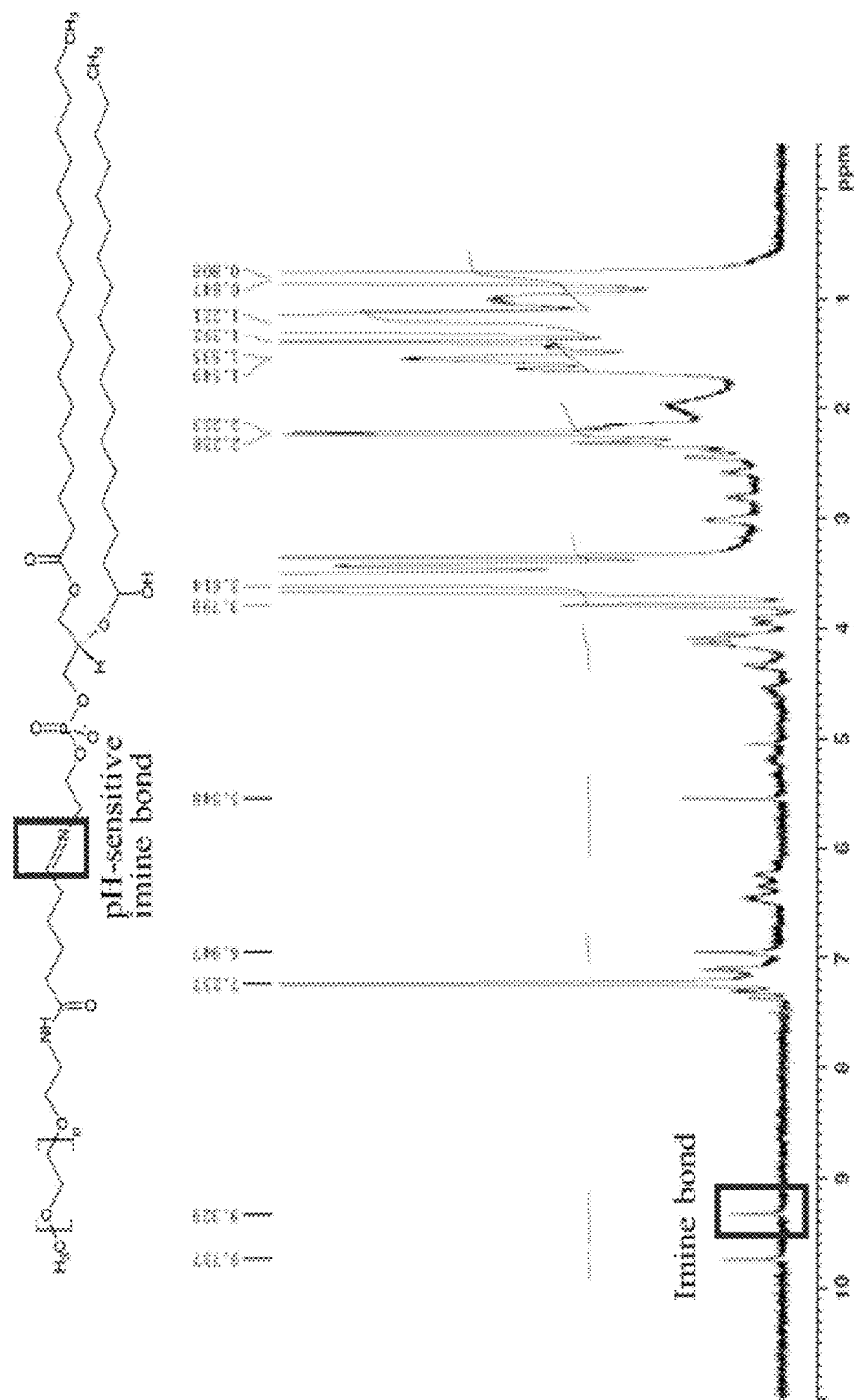
FIG. 1A shows $^1$H NMR of DSPE-imine-omPEG conjugate.
Figure 1B:
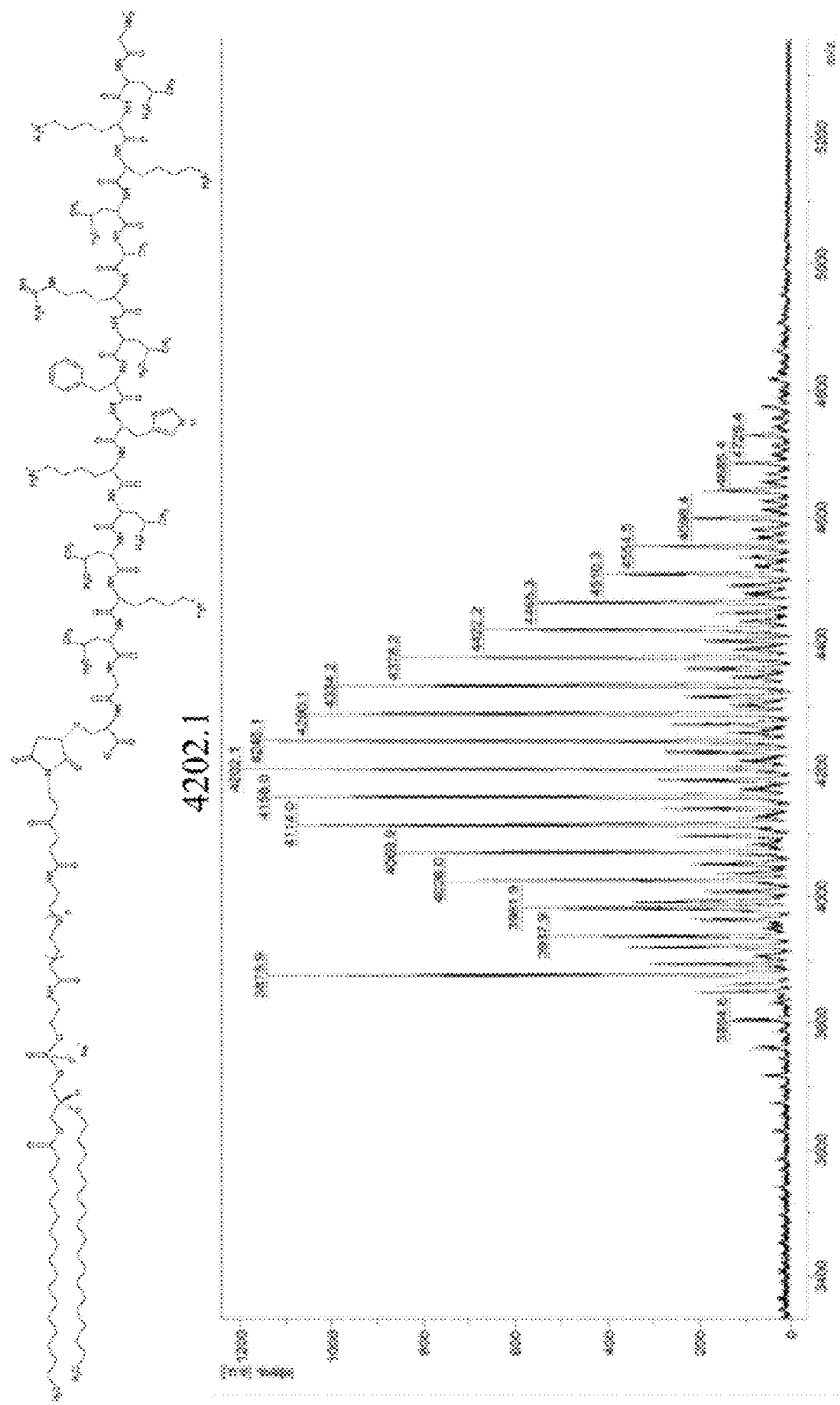
FIG. 1B shows conjugation of DSPE-PEG-maleimide to RF. The structure of the corresponding peptide-conjugates of DSPE-PEG-RF as detected by MALDI-TOF mass spectrometer.
Figure 1C:
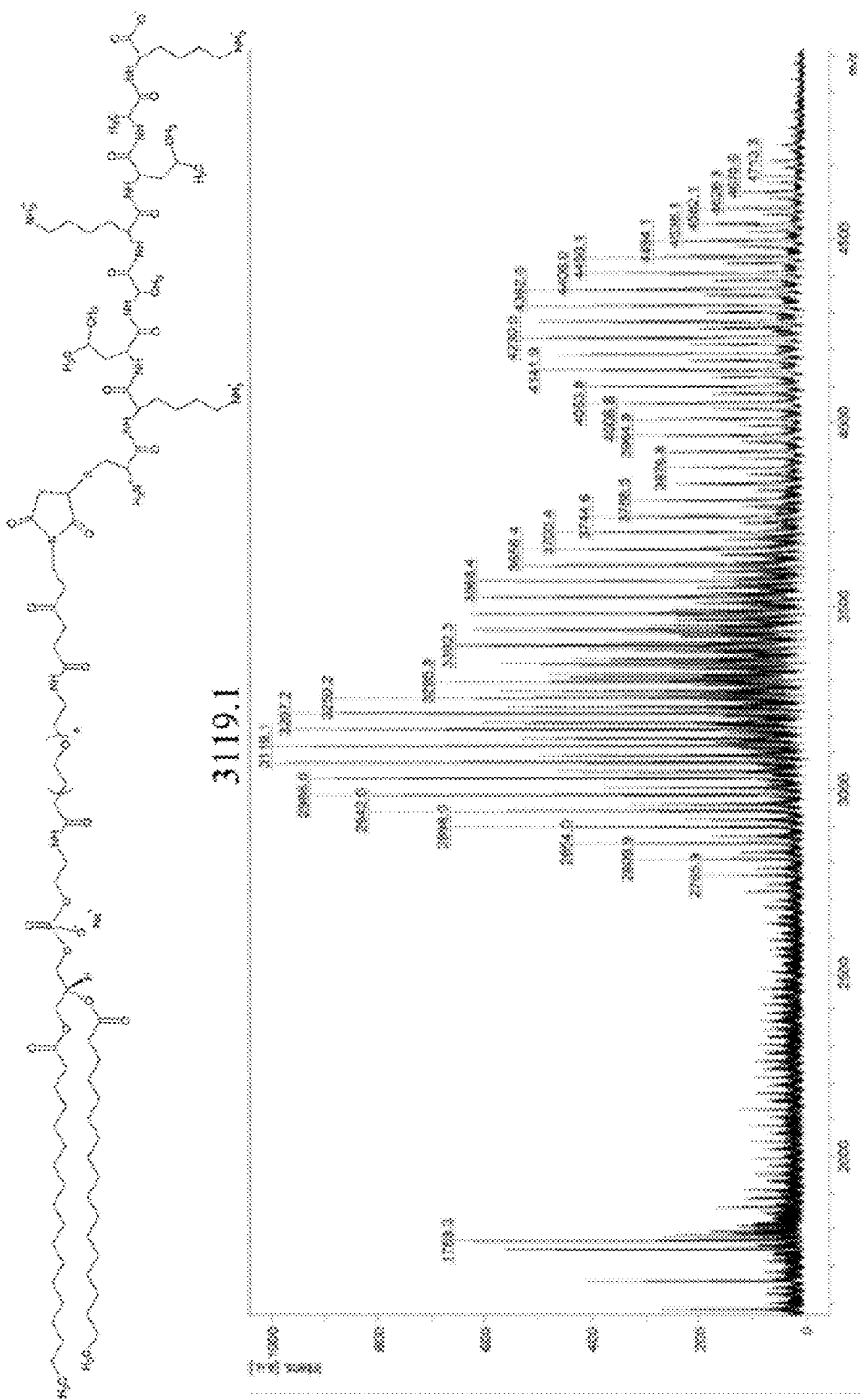
FIG. 1C shows conjugation of DSPE-PEG-maleimide to K. The structure of the corresponding peptide-conjugates of DSPE-PEG-K as detected by MALDI-TOF mass spectrometer.
Figure 1D:
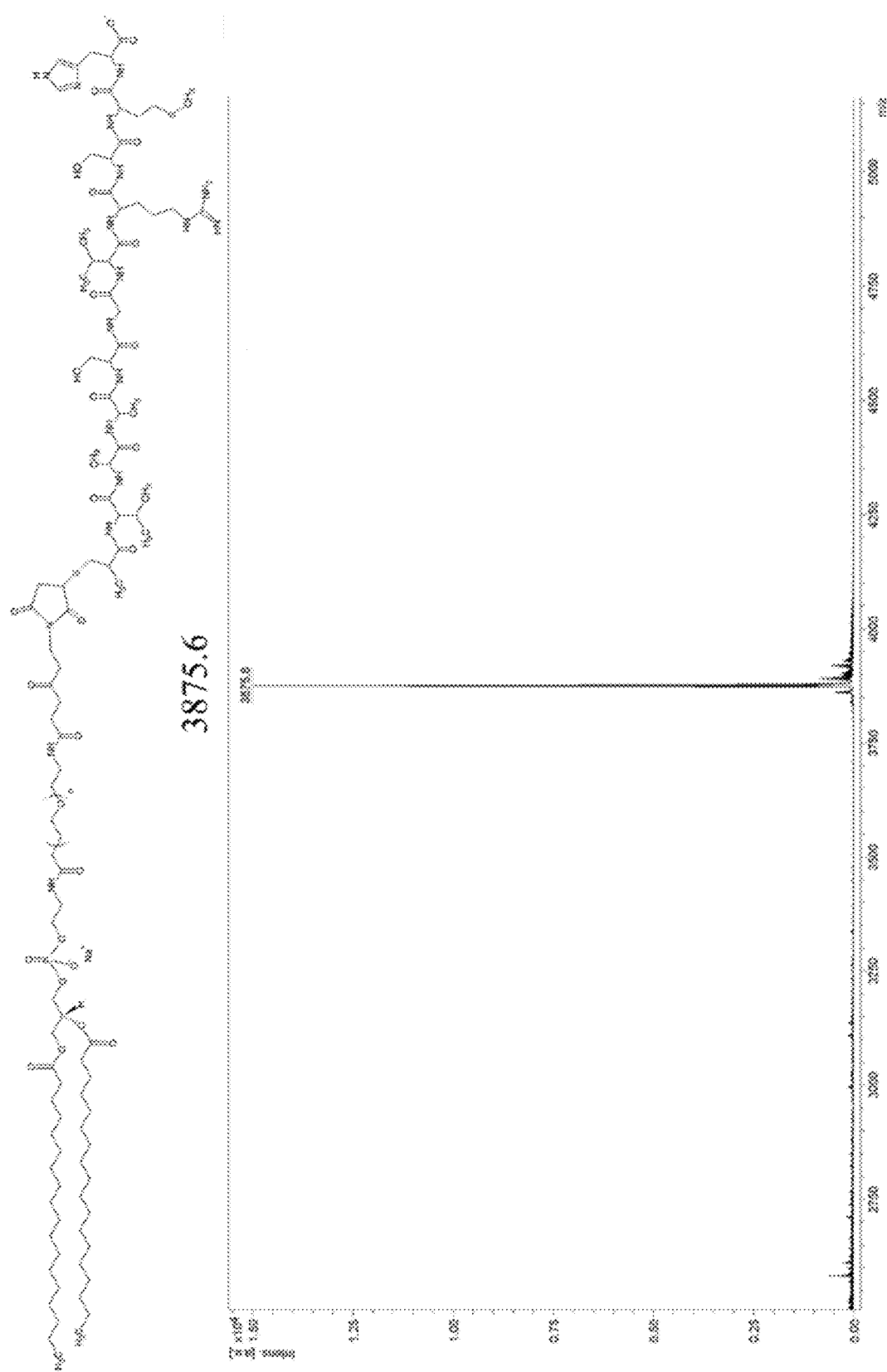
FIG. 1D shows conjugation of DSPE-PEG-maleimide to H. The structure and mass spectra of the corresponding peptide-conjugates of DSPE-PEG-H as detected by MALDI-TOF mass spectrometer.
Figure 2:
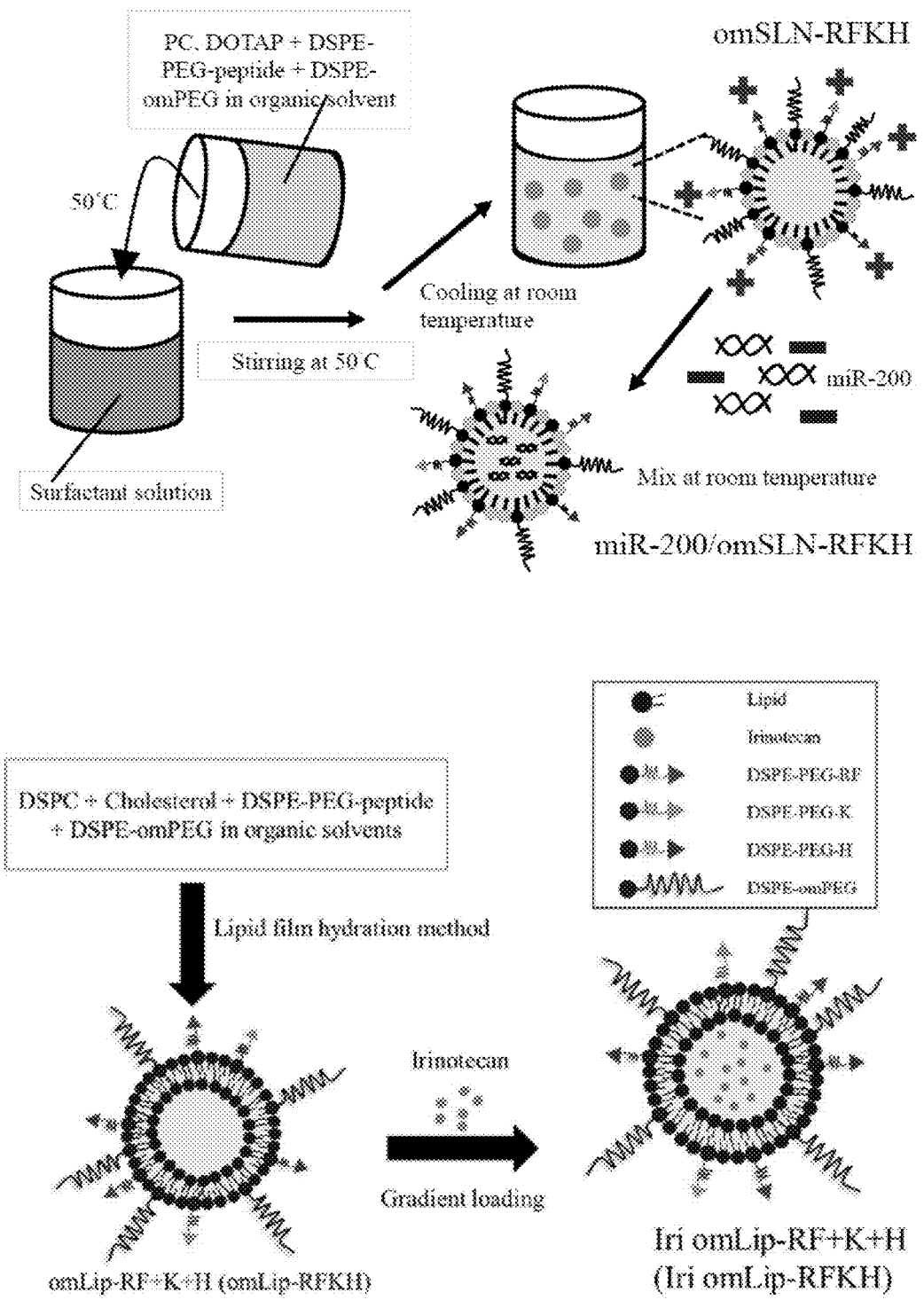
FIG. 2 shows a schematic diagram for the preparation of pH-sensitive and peptide-modified solid lipid nanoparticles (SLN) incorporating miR-200 and pH-sensitive and peptide-modified PEGylated liposomes (Lip) encapsulating irinotecan (Iri), respectively.

Example 1. Synthesis of DSPE-omPEG and DSPE-PEG-Peptide 1,2-Distearoyl-sn-glycero-3-phosphoethanolamine-polyethylene glycol-2000-peptide (DSPE-PEG-peptide) was synthesized by conjugating DSPE-PEG-maleimide to the cysteine residue of peptide RF, K, and H to form a thioether bond. The mass of DSPE-PEG-peptide was confirmed by mass spectrometry, suggesting that the indicated peptides were conjugated to DSPE-PEG (FIG. 1B-1D, FIG. 2 and FIG. 3). Moreover, according to $^1$H NMR analyses, the spectrum of DSPE-imine-omPEG displayed an extra peak at 9.33 ppm (FIG. 1A) compared with the spectra of omPEG and DSPE, indicating that the pH-sensitive imine bond was formed between DSPE and omPEG.

Figure 3:
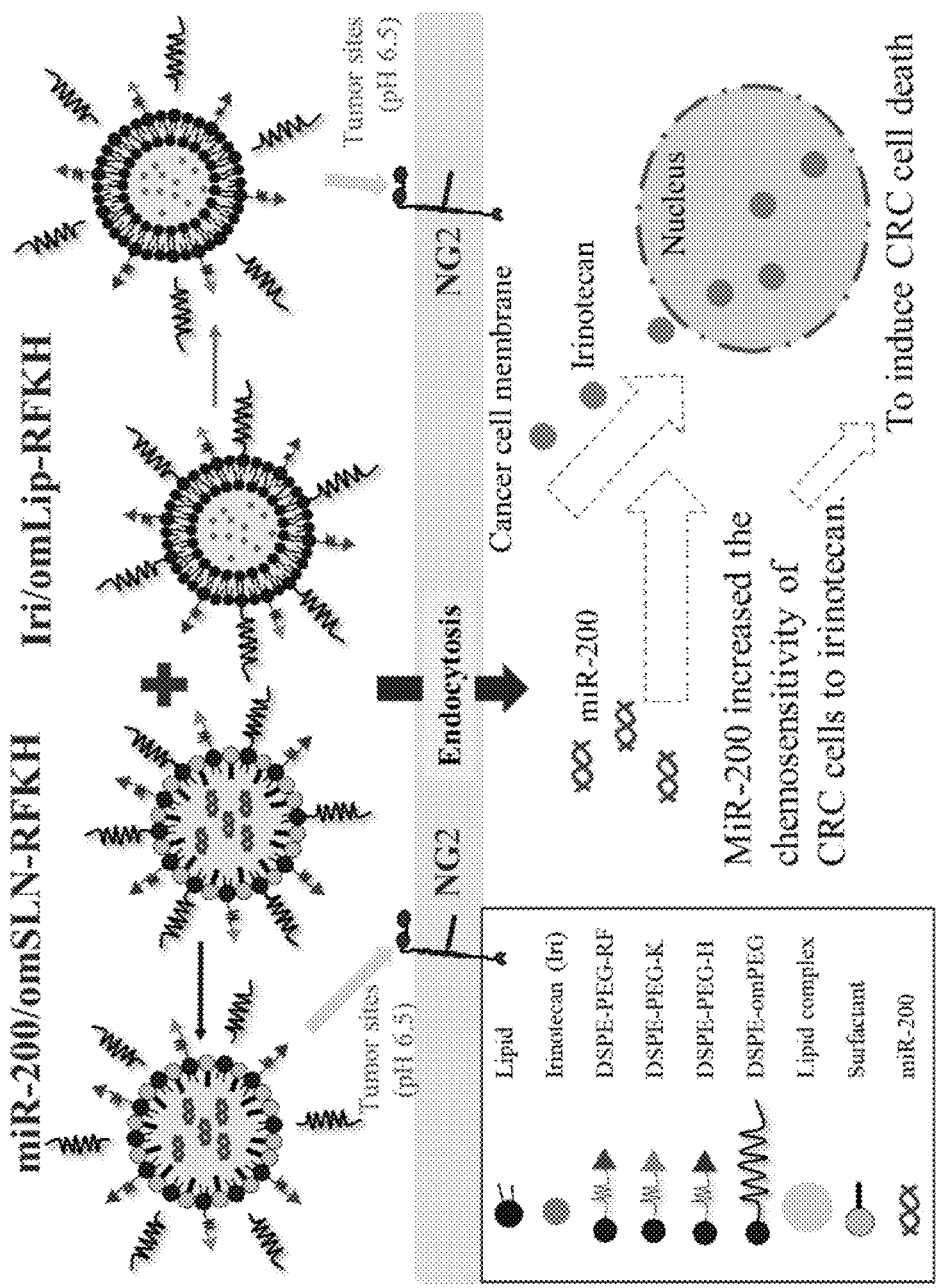
FIG. 3 shows a schematic diagram for the design of pH-sensitive and peptide-modified PEGylated liposomes (Lip) and solid lipid nanoparticles (SLN) incorporating irinotecan (Iri) and miR-200, respectively.

Furthermore, these nanoparticles were well-coated and shielded by outer pH-sensitive PEG layer (FIG. 3).

Example 2. Characterization of Multifunctional Lip and SLN

Preparation of Irinotecan-Loaded Lip

Lip were prepared via the thin film hydration method. Briefly, DSPC, cholesterol, DSPE-PEG-peptide, and DSPE-omPEG (at a molar ratio of 1:0.1:0.1:0.1:0.1; synthesized as described in the Supporting Information) were dissolved in methanol/dichloromethane (1:9). After removal of organic solvent, the lipid film was resuspended in PBS. The mixture was extruded through 400-nm, 200-nm, and 100-nm membrane filter. For preparation of drug-loaded Lip, irinotecan was added to the blank liposomes using an ammonium sulfate gradient method to obtain irinotecan-loaded liposomes.

Preparation of miR-Incorporated SLN

Solid lipid nanoparticles were prepared by aqueous solvent diffusion. L-α-Phosphatidylcholine (PC) or monoglyceride, cholesterol, DOTAP, DSPE-PEG-peptide, and DSPE-omPEG at a molar ratio of 1:0.1:0.1:0.1:0.1, respectively, were dissolved in methanol/dichloromethane (1:9). The resulting mixture was then dispersed rapidly into Tween 80 solution with stirring. Then, miRNA solution was added to the SLN colloidal dispersion, and the mixture was incubated at room temperature for 30 min.

Characterization of Lip and SLN

The size distribution and zeta potential were measured using a Zetasizer (Malvern). The morphology of Lip and SLN was observed under a transmission electron microscope (TEM; JEOL). Additionally, the morphology was detected using a cryo-TEM instrument (FEI).

Encapsulation Efficiency (EE %) and Drug Loading Capacity (DL %).

After centrifuge, irinotecan or miR in both the filtrate and nanoparticles was analyzed via HPLC (Hitachi). The flow rate was 1.0 mL/min and the detection wavelength was 220 nm. EE % and DL % were calculated using the equation shown below.

$$EE\% = [(W_e - W_f)/W_e] \times 100\% \quad (1)$$

$$DL\% = [(W_e - W_f)/W_t] \times 100\% \quad (2)$$

where $W_e$ is the weight of added irinotecan or miR, $W_f$ is the weight of irinotecan or miR in the filtrate, and $W_t$ is the total nanoparticle weight.

MicroRNA Protection Assay

Different formulations of miR in SLN were incubated with 1% RNase or FBS at 37° C. for 24 hours. After incubation, gel retardation assay was performed to analyze all the samples. The samples were run by 5% agarose gel at 120 V for 30 minutes. The gel was visualized and scanned by a gel documentation system (DigiGel; TopBio, Taipei, Taiwan).

Figure 4A:
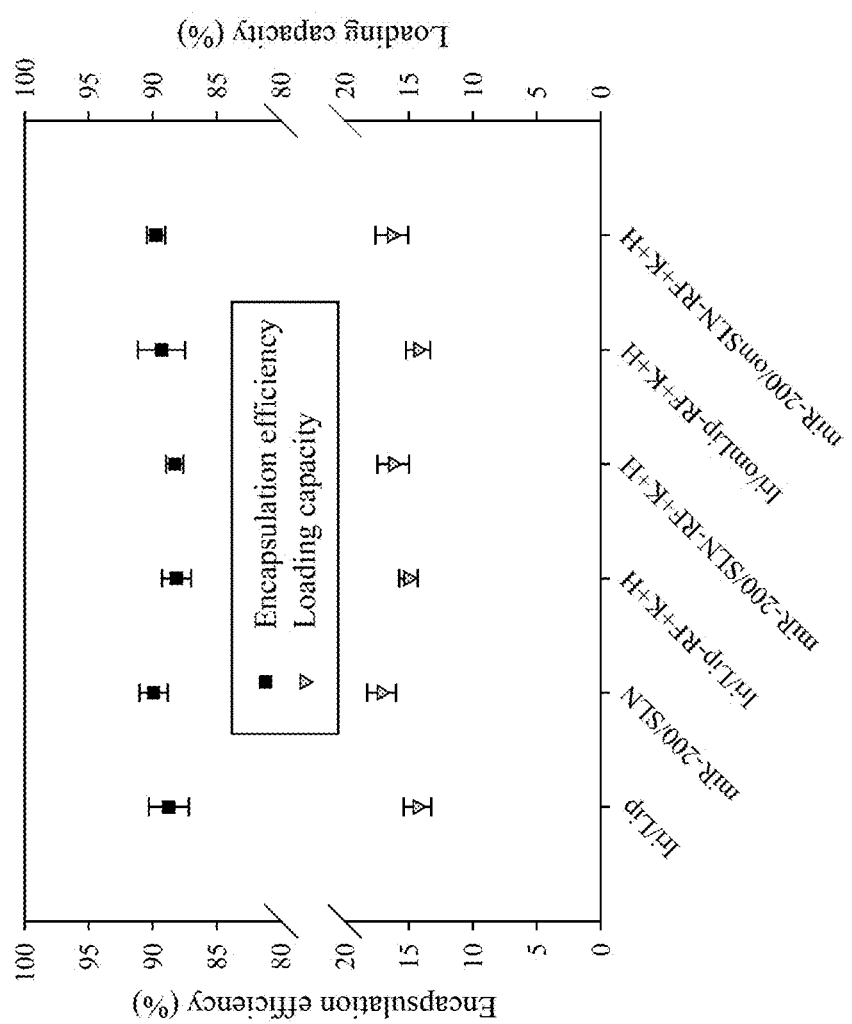
FIG. 4A shows characterization of various formulations. Encapsulation efficiency % and loading capacity %.

Iri/omLip-RFKH and miR-200/omSLN-RFKH displayed a homogeneous and narrow size distribution (Table 1). The liposomes were negatively charged and the SLN were positively charged (Table 1). Encapsulation efficiency % of Iri- or miR-loaded Lip or SLN were all above 88% and the corresponding drug loading capacity % were higher than 14% (Table 1 and FIG. 4A).

TABLE 1

Characterization of peptide-modified liposomes incorporating irinotecan and solid lipid nanoparticles (SLN) encapsulating miR-200 (n = 3; values are mean ± SD).

| | Size (nm) | PDI | Zeta potential (mV) | Encapsulation efficiency % | Drug Loading capacity % |
|---|---|---|---|---|---|
| Iri/omLip-RFKH | 174.7 ± 1.13 | 0.11 ± 0.02 | −8.27 ± 2.19 | 89.32 ± 1.84 | 14.28 ± 0.95 |
| miR-200/ omSLN-RFKH | 141.7 ± 3.75 | 0.12 ± 0.03 | 18.2 ± 1.25 | 89.73 ± 0.71 | 16.34 ± 1.28 |

Figure 4B:
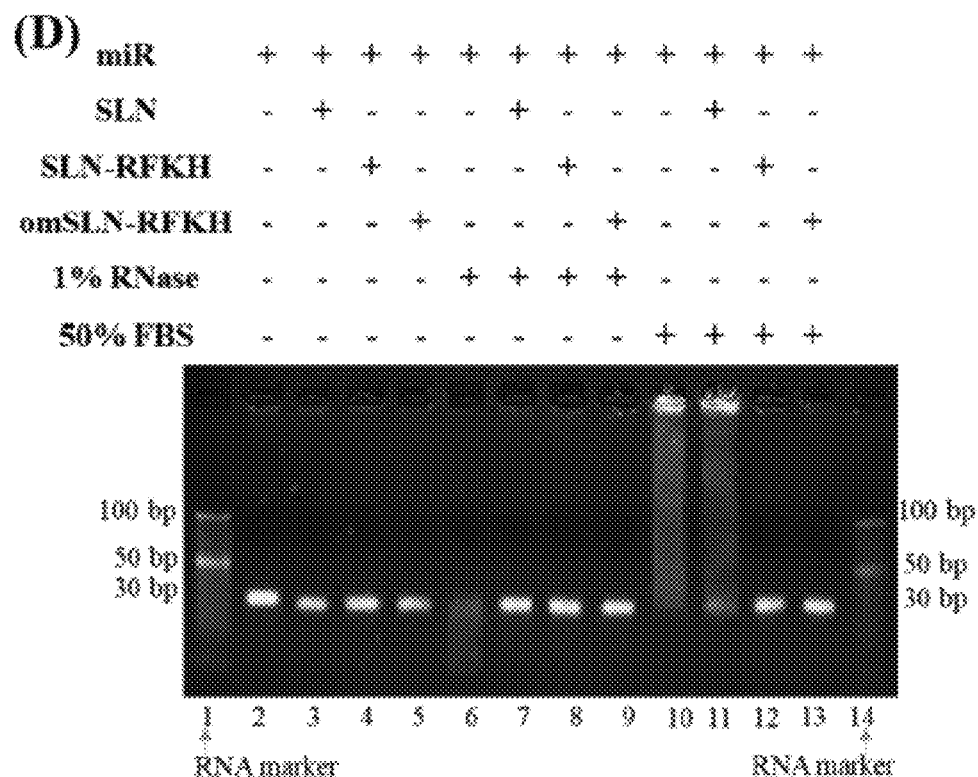
FIG. 4B shows characterization of various formulations. Serum protection test of miR samples was monitored after incubation with 1% RNase or 50% FBS for 24 h. Lanes 2-5: no treatment; Lanes 6-9: 1% RNase treatment; Lanes 10-13: 50% FBS treatment; Lane 1 and 14: RNA marker.
Figure 4C:
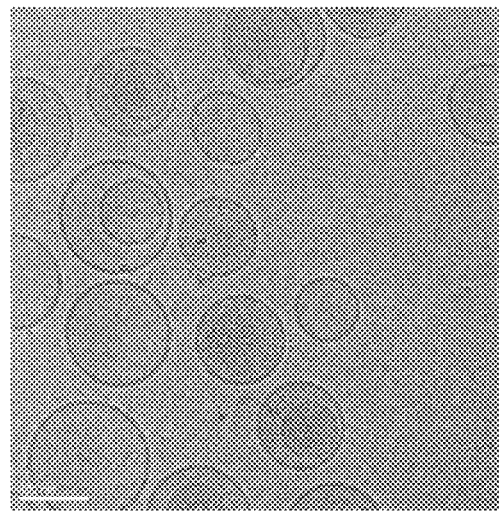
FIG. 4C shows characterization of various formulations. Cryo-TEM images of Iri/omLip-RFKH. Bar=100 nm. For each group, n=3. The representative image is shown.

We found that the particle size and zeta potential of these nanoparticles remained constant with a narrow size distribution (PDI~0.1) after storage at 4° C. for 28 days. Furthermore, naked miR was degraded or aggregated after incubation with 1% RNase or 50% FBS for 24 h, as shown by running agarose gel electrophoresis (FIG. 4B; Lane 6 and 10). Remarkably, the miR samples were well protected by omSLN-RFKH from degradation or aggregation by RNase or FBS (FIG. 4B; Lane 9 and 13). Interestingly, SLN-RFKH without pH-sensitive layer might also provide the similar protection under the attack of 50% FBS (FIG. 4B; Lane 12). However, SLN without pH-sensitive layer and peptide-modification did not prevent miR from degradation or aggregation by the attack of 50% FBS (FIG. 4B; Lane 11), even though SLN with or without modification protected the miR degradation induced by 1% RNase (FIG. 4B; Lane 7-9). Additionally, the liposomes showed spherical particles and no large aggregates were found, as demonstrated by TEM and cryo-TEM (FIG. 4C). The outer layer exhibited the typical bilayer structure of liposomes and crystals of irinotecan were observed in the core, as shown in the cryo-TEM images (FIG. 4C).

Figure 6A:
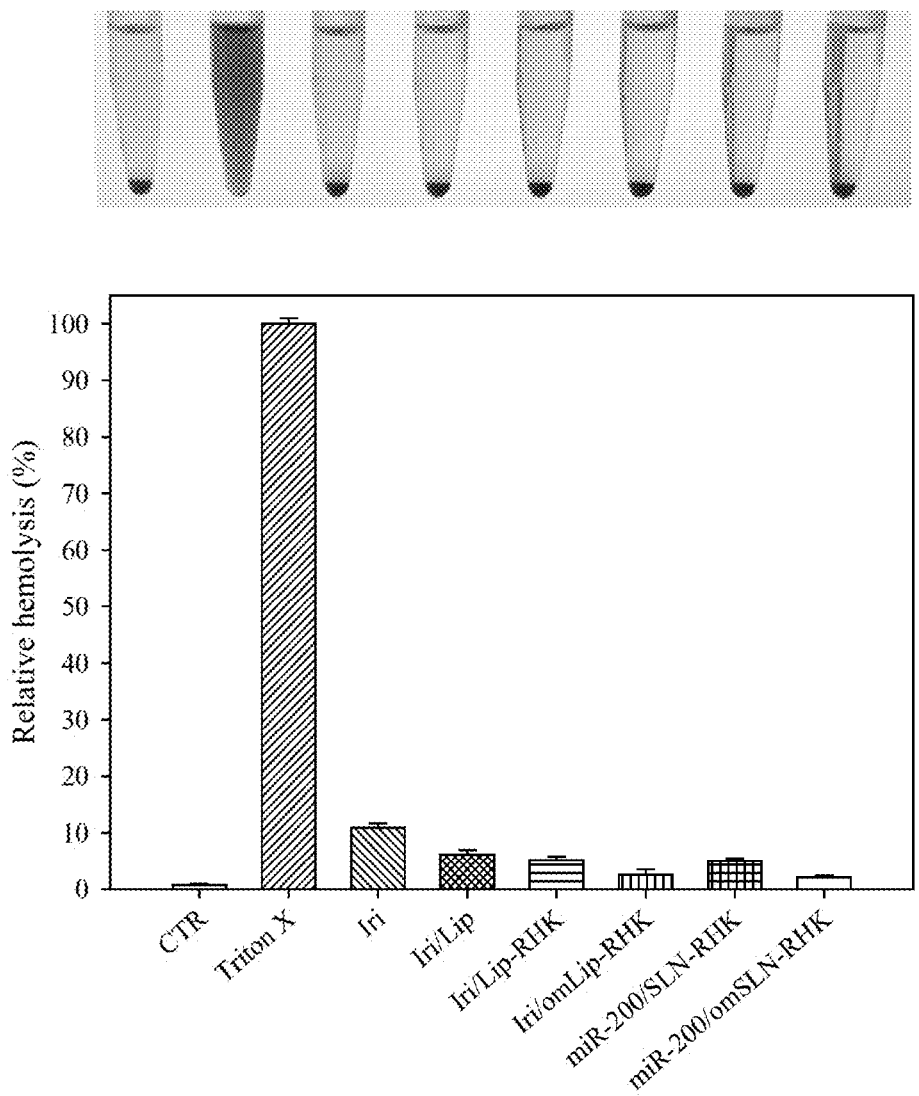
FIG. 6A shows cytotoxicity of various formulations on red blood cells. Hemolysis effect of various formulations (upper panel). Hemoglobin release from rat blood cells was calculated (lower panel). *P<0.05 compared to CTR. †P<0.05 compared to Iri/Lip. ‡P<0.05 compared to Iri/Lip-RFKH. NC: scrambled miRNA.

Especially, miR was protected by pH-sensitive PEG and/or peptide modification in omSLN-RFKH from degradation or aggregation by the attack of RNase or extreme high concentration of FBS (FIG. 4B), indicating that these pH-responsive and peptide-conjugated nanoparticles may provide an excellent platform for the parenteral administration of gene therapeutics such as miR. RF peptide possesses better cell selectivity than TAT peptide, a well-known CPP, by showing lower uptake into normal cells and higher uptake into tumor cells. In our previous study, gefitinib encapsulation in PEGylated liposomes with surface modification by RF enhanced gefitinib transport across the blood-brain barrier (BBB) by modulating the transcytosis pathway(s) and thus further increased gefitinib cytotoxicity against lung cancer cells. Additionally, K peptide triggered the mitochondrial-induced apoptotic pathway and inhibited tumor growth. K peptide also demonstrates the advantages of chemical stability, high anti-proliferation activity and specific disruption of mitochondrial membranes in cancer cells. Moreover, the addition of H peptide can enhance targeting to NG2 overexpressed on tumor vasculature but not on normal vasculature. In the current study, we found that further modification of Iri/Lip-RF with peptide K and H to form Iri/Lip-RF+K+H additionally reduced the viability % of HCT116 cells compared with Iri/Lip-RF (FIG. 6C).

Example 3. Characterization of pH-Responsive Lip or SLN pH-Sensitive Release

Irinotecan- or miR-loaded formulations were placed in a dialysis bag (1,000-3,500 MWCO) and dialyzed separately against PBS at pH 7.4 and 6.5. At the indicated time, solution was withdrawn from the incubation medium. The irinotecan concentrations were determined by HPLC to calculate the cumulative drug release %.

Figure 5A:
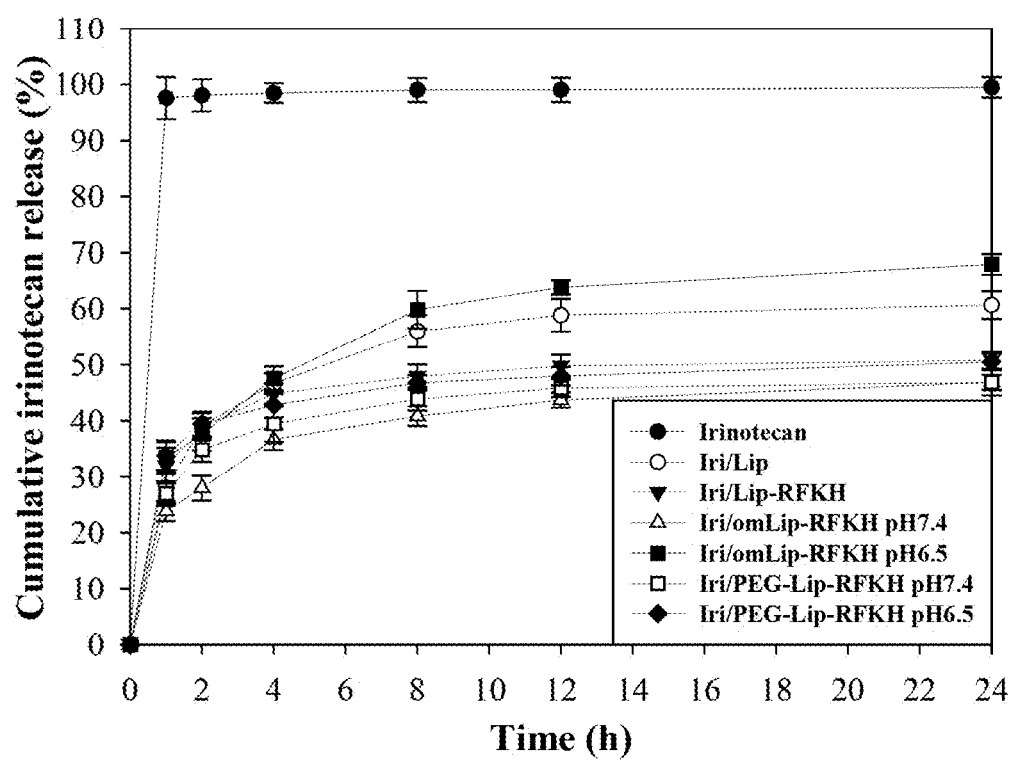
FIG. 5A shows pH-sensitive profiles of various formulations: in vitro release of irinotecan with or without omLip-RFKH at pH 6.5 and 7.4. Iri/PEG-Lip-RKH was prepared by substituting DSPE-imine-PEG5000 into DSPE-PEG5000 (no pH-sensitive imine bond).

For pH-sensitive release of irinotecan or miR at both pH 7.4 and pH 6.5 at 37° C., more than 95% of irinotecan or miR was released from irinotecan or miR solution (as control) during the first 1 h, and the release reached 100% within 24 h (FIG. 5A). However, the percentage of irinotecan released from omLip-RFKH up to 24 h was 46.86±2.34% at pH 7.4, which was increased to 67.89±1.88% at pH 6.5 (FIG. 5A). Thus, omLip exhibited a sustained irinotecan release profile at pH 7.4 and a significant increase under mimic acidic tumor pH. Additionally, nanoparticles prepared with DSPE-PEG5000 without the formation of imine bond (Iri/PEG-Lip-RFKH) were also used for comparison. The release trend of irinotecan from Iri/PEG Lip-RFKH at both pH 6.5 and 7.4 were similar to that of omLip-RFKH at pH 7.4, suggesting no pH-dependent release for Iri/PEG Lip-RFKH (FIG. 5A). Importantly, the release profile of miR from omSLN-RFKH at pH 6.5 and 7.4 also displayed the similar pH-responsive trend as that of Iri/omLip-RFKH, indicating the pH-sensitive de-shielding of omLip or omSLN formulation at pH 6.5 to expose the inner Lip-RFKH or SLN-RFKH for release of irinotecan or miR (FIG. 5A).

Figure 5B:
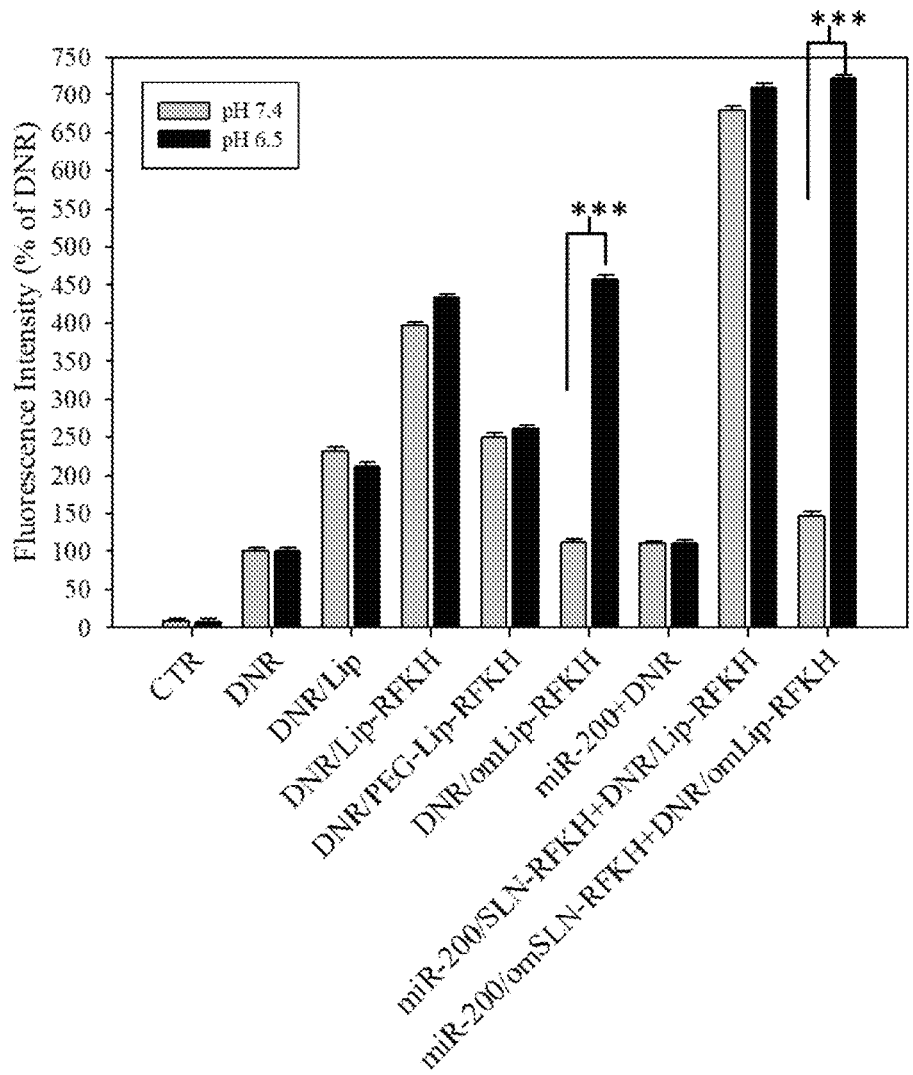
FIG. 5B shows pH-sensitive profiles of various formulations: measurement of cellular uptake of daunorubicin (DNR; a probe of irinotecan) in various formulations into HCT116 cells at pH 6.5 and 7.4 by flow cytometry.

Furthermore, DNR (a probe for irinotecan) in omLip-RFKH showed a much higher cellular uptake after incubation in PBS at pH 6.5 than at pH 7.4 (FIG. 5B). The addition of miR-200/omSLN-RF+K+H further enhanced the intracellular accumulation of DNR from omLip-RFKH at pH 6.5. Interestingly, without the impedance of omPEG long-chain, the combined treatment of Iri/Lip-RF+K+H and miR-200/SLN-RF+K+H displayed the high cellular uptake into human colorectal cancer HCT116 cells at pH 6.5 and pH 7.4 (no imine bond; FIG. 5B). However, there was no pH-responsive cellular uptake of DNR from PEG-Lip-RFKH (no imine bond; FIG. 5B). Moreover, the CLSM results shown revealed that after 24 h of incubation, DNR from the pH-responsive omLip-RFKH was predominantly localized in the nucleus of HCT116 cells at pH 6.5, which confirmed the final destination of the topoisomerase inhibitor carried by omLip-RFKH into the nucleus to induce cytotoxicity. We further verified that DNR in Lip-RFKH was escaped from endosomes and targeted to mitochondria at 30 min. DNR was then transported into the nucleus after 3 h-delivery and maintained in the nucleus up to 24 h after incubation of HCT116 cells with DNR/Lip-RFKH.

Figure 5C:
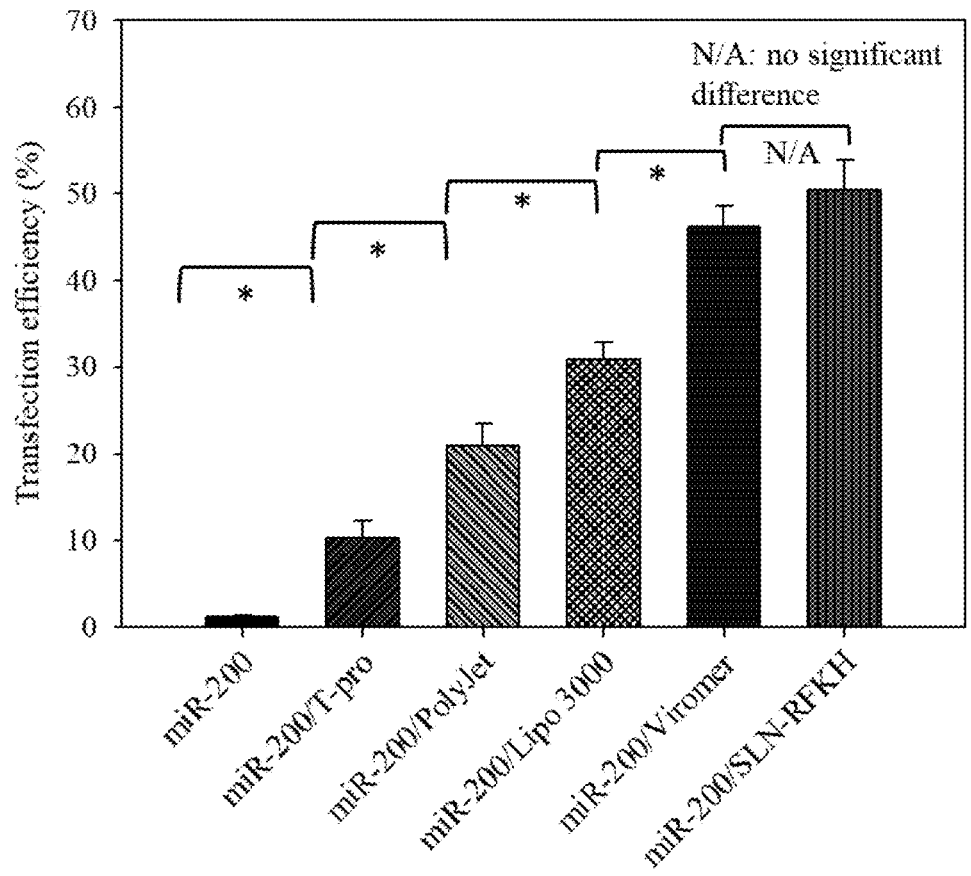
FIG. 5C shows pH-sensitive profiles of various formulations: transfection efficiency % of FAM-miR-200 by SLN-RFKH and commercial reagents in HCT116 cells by flow cytometry. *P<0.05

The pH sensitivity of omLip-RFKH and omSLN-RFKH was confirmed by findings of the cumulative release (FIG. 5A), cellular uptake (FIG. 5B), and intracellular localization (FIG. 5C). However, there was no pH-dependent release or cellular uptake of Iri, DNR or miR from PEG-Lip-RFKH or PEG-SLN-RFKH (no imine bond; FIG. 5A-B). We thus suggest that omLip-RFKH might function as a tumor-selective delivery system that decreases entry of therapeutics into normal tissues (pH 7.4) and increases their uptake at acidic tumor sites (pH 6.5). A similar finding using other pH-sensitive carriers has been reported in a previous study. Moreover, when we observed the CLSM images, most DNR (a probe for irinotecan) released from omLip-RFKH at pH 6.5 appeared in the nucleus at 24 h, revealing that these peptide-modified nanoparticles tended to successfully avoid drug entrapment by lysosomes and confirming an endosomal escape effect in agreement with a former study. The mitochondria-targeting and nuclear localization of DNR/Lip-RFKH in HCT116 cells were further verified using CLSM after 30 min, 3 h, and 24 h-incubation. Consistently, we found that Lip-RFKH was preferentially taken up by HCT116 cells through clathrin-dependent and adsorptive-mediated endocytosis pathways (Figure S2D), which are reported to be the major endocytosis pathways for liposomes.[28] We suggest that the positively charged RF, H and K peptides on the liposome surface might increase the internalization of nanoparticles through adsorptive-mediated pathway.

Example 4. Endocytosis Mechanisms for Uptake of Peptide-Modified Lip and SLN

Cell Lines

HCT116 and CT26, human colorectal cancer and mouse colon adenocarcinoma cell lines, respectively, were obtained from the Food Industry Research and Development Institute (Hsinchu City, Taiwan). The cells were cultured in Dulbecco's modified Eagle's medium (DMEM) supplemented with 10% fetal bovine serum in an incubator with 5% $CO_2$ at 37° C.

pH-Responsive Cellular Uptake and Intracellular Localization

Daunorubicin (DNR) was used as a fluorescent probe for irinotecan. Accumulation of DNR from different Lip in HCT116 cells was measured and observed using a FACSCalibur flow cytometer (Becton Dickinson) and an Olympus confocal laser scanning microscope (CLSM), respectively. After incubation with different treatments at pH 7.4 and 6.5 for 24 h, the cells were stained with DAPI (Sigma), a nuclear dye. Fluorescence observation was carried out using CLSM. For verification of characteristics of mitochondria-targeting and endosomal escape, a mitochondrial dye, MitoTracker Green (ThermoFisher) and an antibody for early endosome antigen 1 (EEA1; Cell signaling) were used.

According to the results shown in Figure S2D, chlorpromazine (CPZ) and poly-L-lysine exhibited significant decreases in the relative fluorescence intensity % of DiI/Lip-RFKH in HCT116 cells after 3 h-incubation, suggesting that the cellular uptake of DiI/Lip-RFKH was primarily driven by clathrin- and adsorptive-mediated endocytosis, as supported by Figure S2D. Furthermore, the efficiency % of HCT116 cell transfected with FAM-miR-200 by SLN-RFKH at 24 h was significantly greater than of Lipofectamine™ 3000, T-Pro P-Feet, PolyJet™ (served as positive controls) and naked FAM-miR-200, as detected by flow cytometric analysis (FIG. 5C). However, Viromer® displayed a transfection efficiency % compatible with that of SLN-RFKH (FIG. 5C; $P>0.05$). Moreover, upon visualization of the intracellular distribution of FAM-miR200/SLN-RFKH in HCT116 cells at 24 h via CLSM, clear uptake of FAM-miR200 (green fluorescence) was observed in the cytoplasm of HCT116 cells. In addition to miR, the cell nuclei were stained with DAPI (blue), and lysosomes were stained with LysoTracker (red). It was obvious that FAM-miRNA-200 did not colocalize with lysosomes after 24 h of incubation. Endo/lysosomal escape was thus verified, indicating that miR-200 was well-protected by SLN-RFKH to prevent miR-200 from degradation in endo/lysosomes.

The formulation of miR-200/SLN-RFKH improved the poor cellular uptake and enhanced the endosomal escape of miR-200, as validated in FIG. 5C. Excitingly, the transfection efficiency % of SLN was greater or equal to that of commercial available Lipofectamine™, PolyJet and Viromer® (FIG. 5C). The electrostatic interaction between the negative charges of miR-200 and the positive charges in SLN-RFKH allowed the formation of a stable complex. Another advantage of cationic nanoparticles is efficient endosomal escape via the proton sponge effect, leading to destabilization of endosomal membranes and improvement of gene transfer efficiency.[29] FAM-miR-200 (green) observed via CLSM was not colocalized with LysoTracker (red), indicating a good endosomal escape effect of miR-200 from SLN-RFKH to prevent miR damage in lysosomes.

Example 5. Toxicity of Iri- or miR-Loaded Lip or SLN on Blood Cells, Intestinal Cells, and Cancer Cells Cell Viability The cytotoxicity of formulations in rat small intestinal epithelial IEC-6 cells and human colorectal cancer HCT116 cells was determined using a sulforhodamine B (SRB) assay. After 48-h incubation with various formulations, the cells were stained with SRB for 10 min. The absorbance at 540 nm was detected with a microplate TECAN reader.

Nanoparticles were usually administered clinically by injection. Hence, hemolysis of Iri/Lip or miR/SLN was investigated using rat blood cells as a safety evaluation. As shown in FIG. 6A, various Iri/Lip or miR/SLN formulations induced little hemolysis (3%-7%), revealing the acceptable safety of these tested liposomal and SLN formulations. Therefore, these modifications caused relatively low toxicity to blood cells. However, irinotecan showed ≈10% hemolysis, indicating slight toxicity (FIG. 6A). Furthermore, irinotecan solution displayed ≈30% cytotoxicity to noncancerous IEC-6 cells, but irinotecan in Lip and Lip-RFKH reduced the cytotoxicity to about 15%-20%. However, Iri/omLip-RFKH, miR-200 in SLN-RFKH, and omSLN-RFKH all displayed less than 10% toxicity to IEC-6 cells (FIG. 6B), indicating the reduction in toxicity to intestinal epithelial cells. Moreover, irinotecan showed a concentration-dependent inhibition on viability of HCT116 cells and irinotecan at $4\times10^{-6}$ M exhibited ≈20% cytotoxicity in HCT116 cells. Thus, this concentration was chosen to check the improvement by various liposomal formulations and/or combination with miR-200. As shown in FIG. 6C, liposomes modified with RF+K and RF+K+H exhibited more cytotoxicity than liposomes modified with RF alone (both $P<0.05$). The administration of miR-200/SLN-RFKH first and followed by Iri/Lip-RFKH exhibited the greatest inhibition percentage among all the groups (FIG. 6C). Additionally, all the unmodified and peptide-modified Lip and SLN carriers showed marginal hemolysis effect to RBC cells and low cytotoxicity toward IEC-6 and HCT116 cells.

Apoptosis induced through PARP cleavage by irinotecan or its metabolite SN-38 has been demonstrated in colon carcinoma cells. In the present study, combined treatment with miR-200/SLN-RFKH intensified the cytotoxicity of Iri/Lip-RFKH against HCT116 cells (FIG. 6D).

Example 6. Cell Death-Related Mechanisms

Western Blotting

After treatment with different formulations for 48 h, the protein samples were separated via SDS-PAGE and transferred onto a polyvinylidene difluoride membrane (Bio-Rad) at 80 V. After blocking, blots were incubated with primary antibodies from Cell Signaling or Abcam and horseradish peroxidase-conjugated goat anti-rabbit IgG (Jackson) and developed using an detection system (Millipore). The membrane was reprobed with anti-β-actin antibody and monitored using an enhanced chemiluminescence detection kit (PerkinElmer).

Figure 7A:
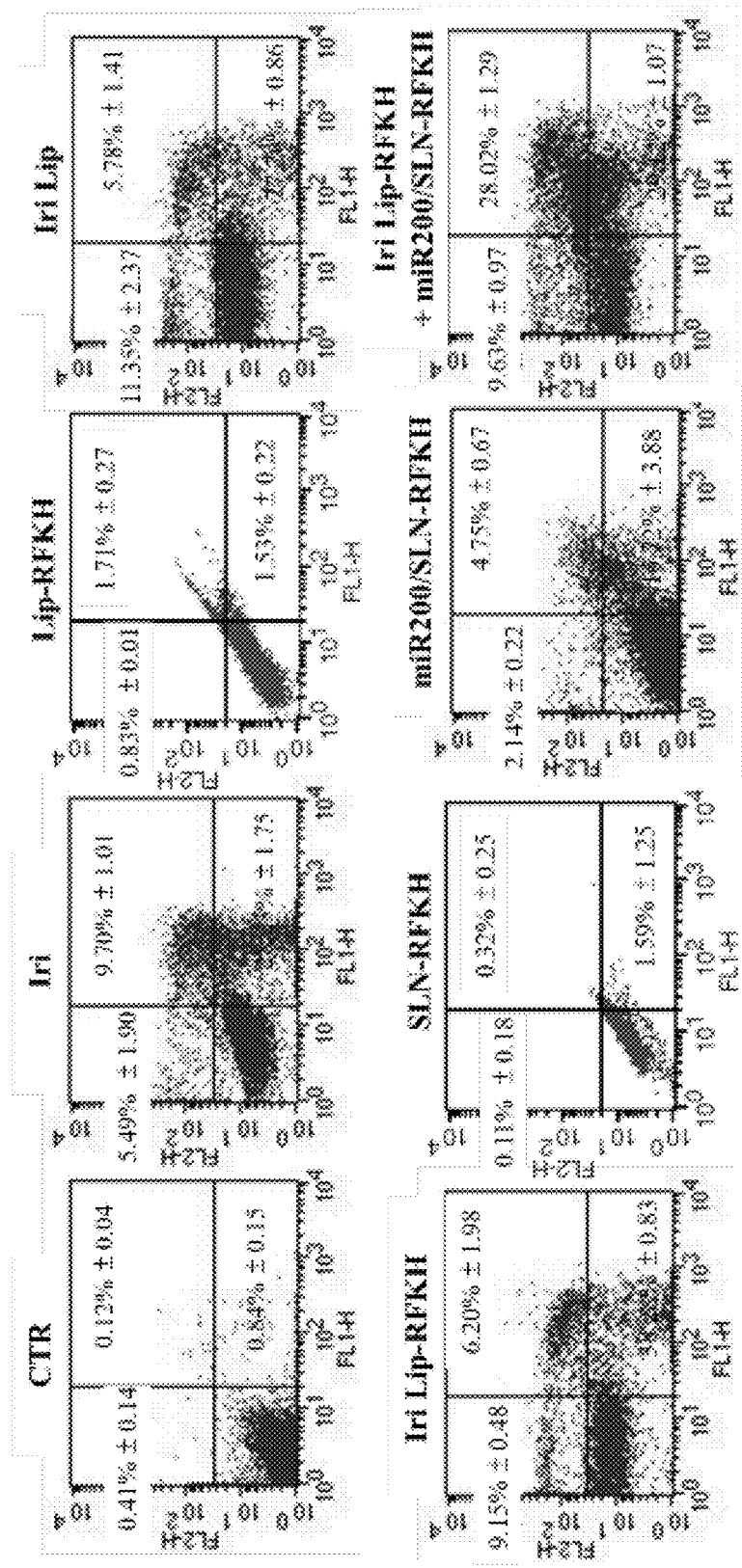
FIG. 7A shows effect of different formulations for 48 h on the cell population distribution of apoptosis and necrosis in HCT116 cells using annexin V/PI assay.
Figure 7B:
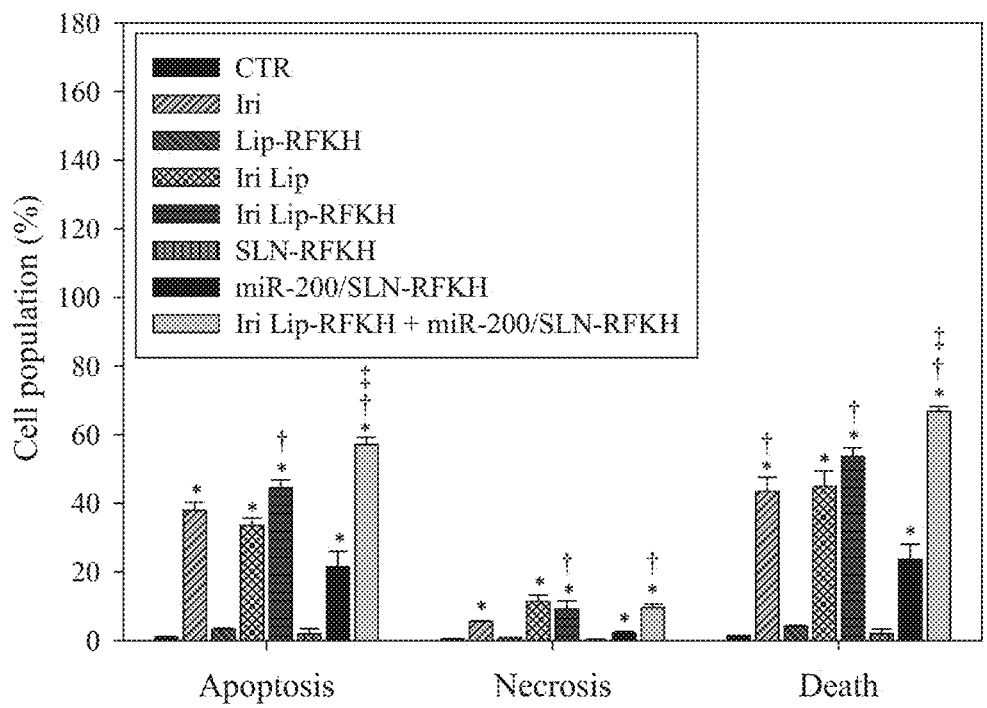
FIG. 7B shows effect of different formulations for 48 h on the relative percentage of apoptosis, necrosis, and death of cell population in HCT116 cells.
Figure 7C:
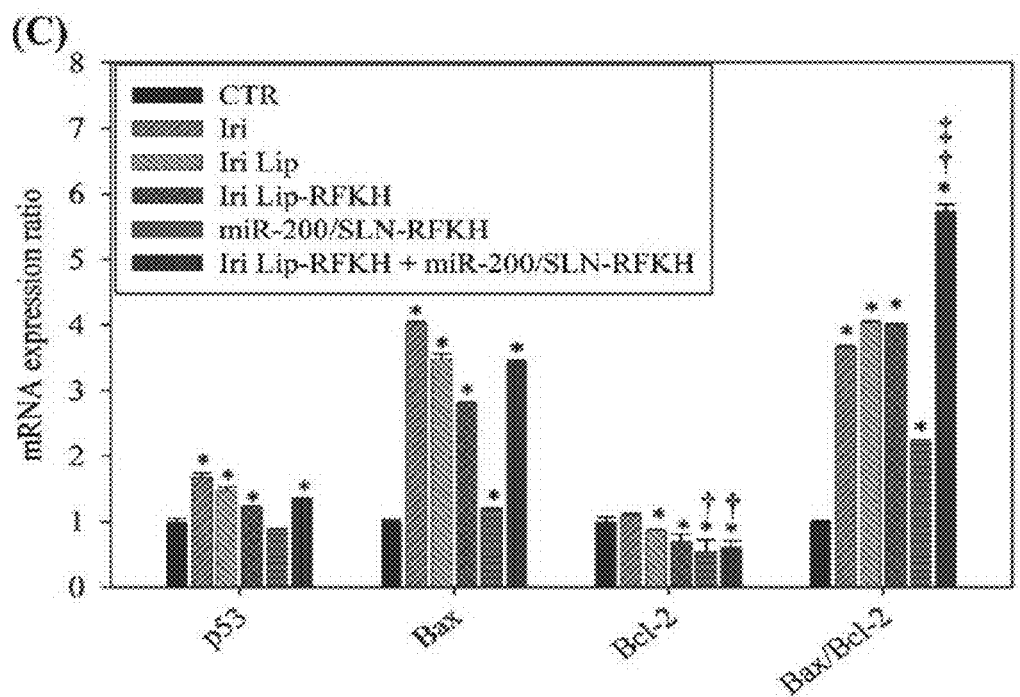
FIG. 7C shows effect of different formulations for 48 h on the mRNA expressions of apoptosis-associated pathway such as p53, Bax, Bcl-2, and ratio of Bax/Bcl-2 in HCT116 cells.
Figure 7D:
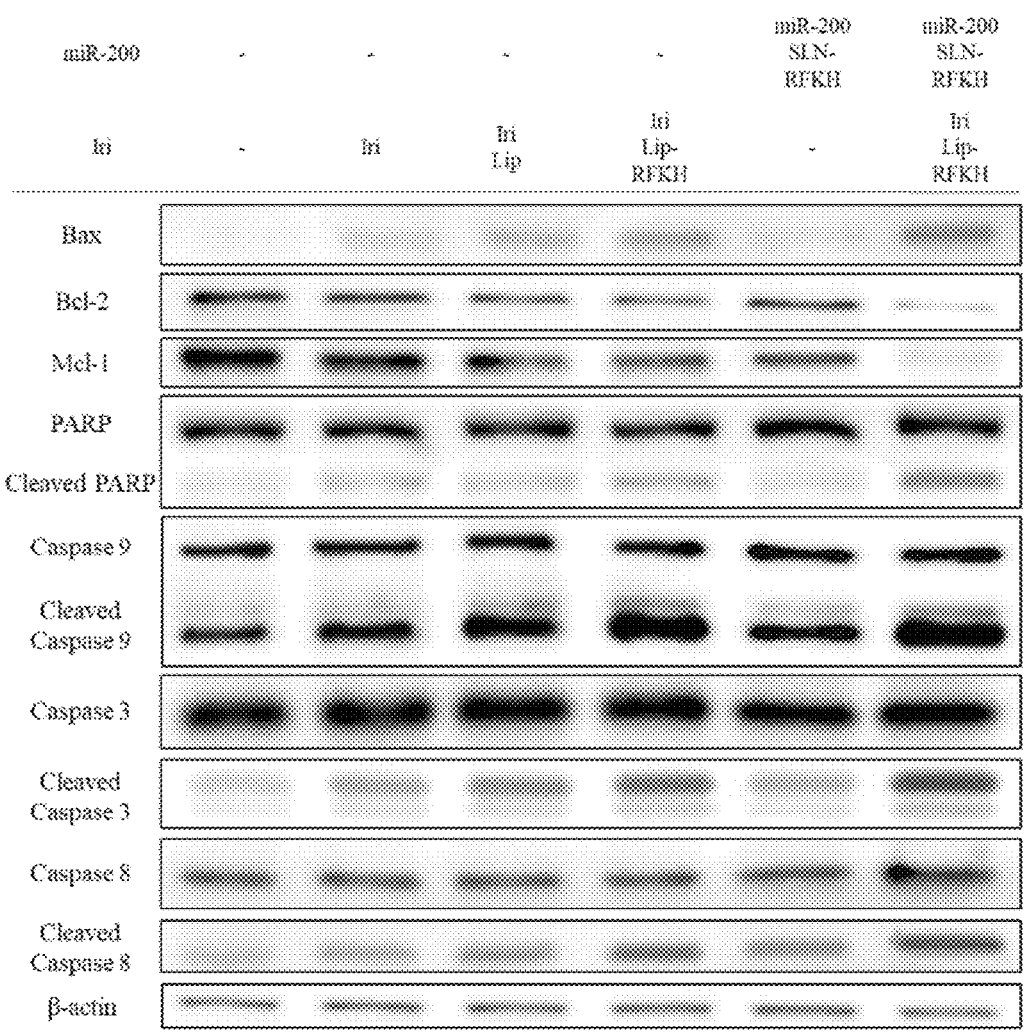
FIG. 7D shows effect of different formulations for 48 h on the protein expressions of apoptosis-associated pathway in HCT116 cells by western blotting.
Figure 7E:
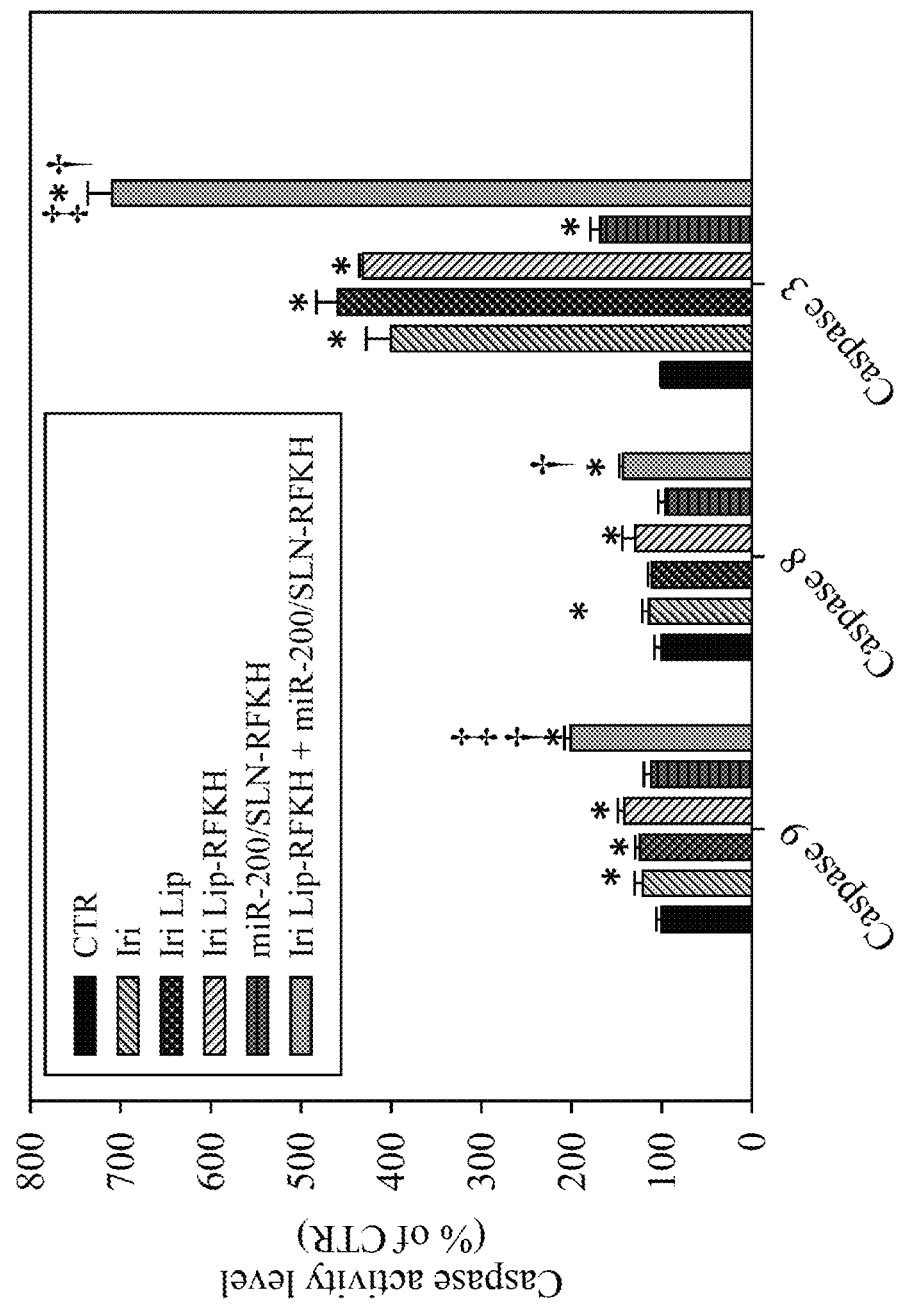
FIG. 7E shows effect of different formulations for 48 h on the activity levels of caspase-3, -8, -9, of apoptosis-associated pathway in HCT116 cells.

The apoptosis percentage (the sum of early and late apoptotic cells) and death percentage (the sum of apoptotic and necrotic cells; FIG. 7A,B) induced by Iri/Lip-RFKH were both much higher than those induced by Iri/Lip. Furthermore, treatment of HCT116 cells with miR-200/SLN-RFKH followed by Iri/Lip-RFKH triggered the greatest induction (%) of apoptosis and cell death in HCT116 cells (FIG. 7A,B). Nevertheless, empty nanocarriers such as Lip-RFKH and SLN-RFKH exhibited negligible apoptosis, necrosis and death % (FIG. 7A,B). Moreover, miR-200/SLN-RFKH+Iri/Lip-RFKH significantly intensified the Bax/Bcl-2 mRNA ratio (FIG. 7C) and considerably upregulated the protein expression levels of Bax, cleaved PARP, and caspase-3, -8, and -9 (FIG. 7D), as well as escalated the caspase-9 and caspase-3 activity levels to the greatest degree (FIG. 7E). In contrast, Mcl-1 and Bcl-2 proteins were remarkably downregulated (FIG. 7D).

Irinotecan-induced tumor cell death primarily occurred via apoptosis induction and partially via necrosis, as supported by our results shown in FIG. 7. Furthermore, the increase in the % of cells undergoing apoptosis and cell death was the most significant in the Iri/Lip-RFKH+miR-200/SLN-RFKH group (FIG. 7A-7B). Previous investigations have indicated that Bax and caspase-9 are involved in triggering apoptosis caused by irinotecan. Consistently, our results showed that the mRNA, protein expression and/or activity levels of Bax, cleaved PARP, and caspase-3 and -9 were highest in the Iri/Lip-RFKH+miR-200/SLN-RFKH group among different treatments (FIG. 7C-7E).

Example 7. In Vivo IVIS and PET/CT Imaging as Well as Antitumor Efficacy and Biosafety Studies Establishment of In Vivo Mouse Tumor Model Male BALB/c mice at the age of 6 weeks with body weights of 20±2 g were purchased from National Laboratory Animal Center (Taipei, Taiwan) and maintained in an individual ventilation cage system. The animals were ensured free access to sterilized food and water. CT-26 ($10^5$ cells in 0.1 ml PBS) were injected subcutaneously into the right flank of mice to obtain tumor-bearing BALB/c mice. All processes performed on the animals were in accordance with the National Institutes of Health Guide for the Care and Use of Laboratory Animals and were approved by the National Yang-Ming University Animal Committee.

IVIS Imaging

CT-26 cells ($10^5$ cells in 0.1 ml PBS) were injected subcutaneously into the right flank of mice to obtain tumor-bearing BALB/c mice. When tumor volume reached approximately 100 mm$^3$ (equation 4), the mice were randomly assigned to six groups (n=5 for each group). Group 1 was treated with saline solution (CTR), group 2: Iri solution, group 3: Iri/Lip, group 4: Lip-RFKH/Iri, group 5: miR-200/SLN-RFKH+Iri/Lip-RFKH (miR-200/SLN-RFKH first followed by Iri/Lip-RFKH), and group 6: miR-200/omSLN-RFKH+Iri/omLip-RFKH. Mice were injected intravenously (IV) with Iri at 100 mg/kg and miR-200 at 1.25 mg/kg in different formulations every 7 days for 28 days. Fluorescence images were visualized one day after the final treatment using an IVIS SPECTRUM (Caliper).

$$V=(L\times W^2)/2 \qquad (4)$$

where length (L, mm) is the longest diameter and width (W, mm) is the shortest diameter perpendicular to the length axis.

Positron Emission Tomography/Computed Tomography (PET/CT)

Tumor images were monitored using PET/CT. One day after the final treatment (at day 28), mice were injected intravenously with 0.282 mCi [$^{18}$F]-fluorodeoxyglucose ($^{18}$F-FDG). Images were acquired using a LabPET/X-SPECT/X-O CT imaging system (TriFoil Imaging, Inc., USA) at 30 min after injection of $^{18}$F-FDG. In addition, CT acquisitions were conducted for 3 min (FOV=80 mm) after each PET scan to detect anatomical information for each animal and construct an attenuation map for further image restoration. PET and CT images were observed and computed using AMIDE software (SourceForge, Iowa, USA).

Assessment of In Vivo Antitumor Efficacy and Body Weight.

Animal body weight and tumor size were detected every 3 or 4 days for 28 days. Tumor size was measured with a digital caliper and the tumor volume (V) was calculated (equation 4).

Figure 8A:
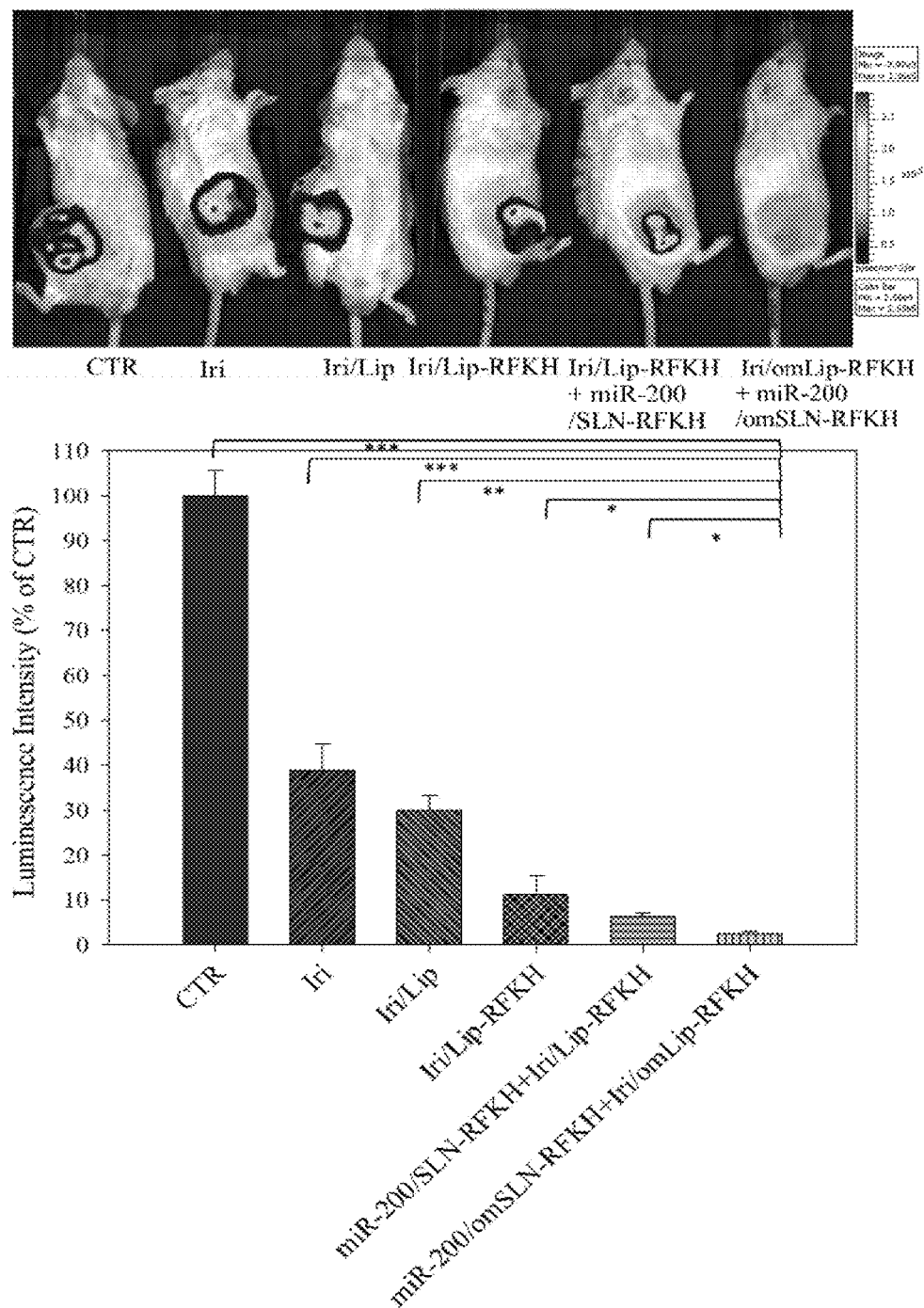
FIG. 8A-8D shows 8A) CT26-bearing mice were administered with various formulations once a week for 28 d. IVIS images of the mice in different groups were taken at the treatment end of 28 d. n=5; the relative bioluminescence intensity is displayed in the lower panel. 8B) PET/CT images of the representative mice from each group. White circles: tumor; yellow circles: bladder; orange circles: heart. 8C) Tumor size and 8D) body weight as a function of time in CT-26 bearing mice. *P<0.05; P<0.01; *P<0.001.

Mice bearing colorectal CT26 tumor cells without treatment (CTR) displayed high fluorescence in the tumor region as shown by the IVIS images (FIG. 8A). Furthermore, the images were normalized by IVIS software and the relative bioluminescence intensity is displayed in the lower panel of FIG. 8A. Moreover, we used $^{18}$F-FDG as a tool for detecting tumor proliferation change by PET/CT (FIG. 8B) and 3D PET imaging. The CT26 tumor-bearing mice treated with different Iri/Lip-RFKH and/or miR-200/SLN-RFKH formulations exhibited decreases in fluorescence and $^{18}$F-FDG signals to various degrees around the tumor (FIG. 8AB), while the mice treated with omLip-RFKH/Iri+omSLN-RFKH/miR-200 showed the most significant reduction in tumor fluorescence and $^{18}$F-FDG retention (FIG. 8AB). Moreover, the tumor size treated with pH-sensitive omLip-RFKH/Iri+omSLN-RFKH/miR-200 was 49.12%±5.83% of the original tumor volume on day 28, which was superior to all other treatments (FIG. 8C).

Figure 8B:
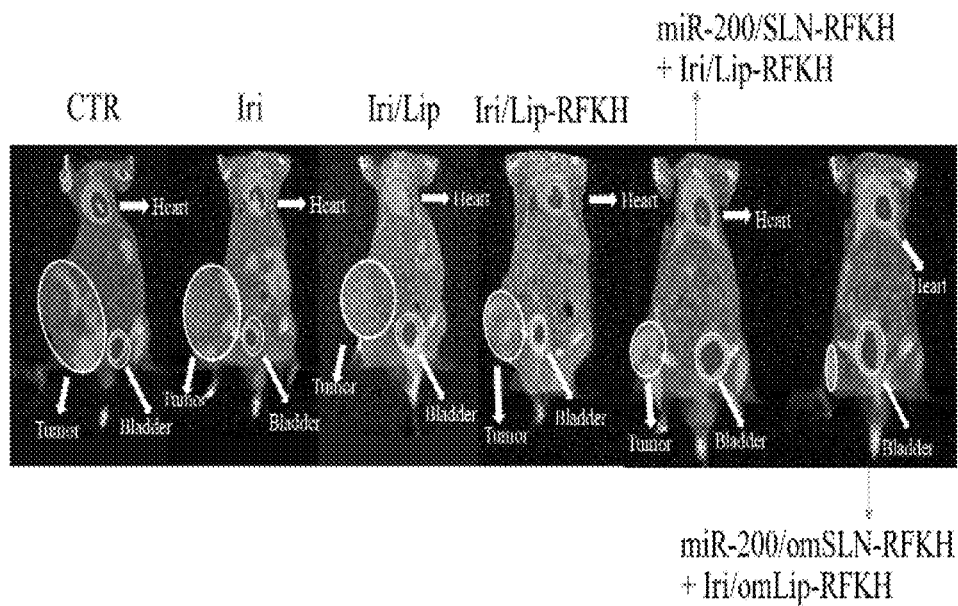
Figure 8C:
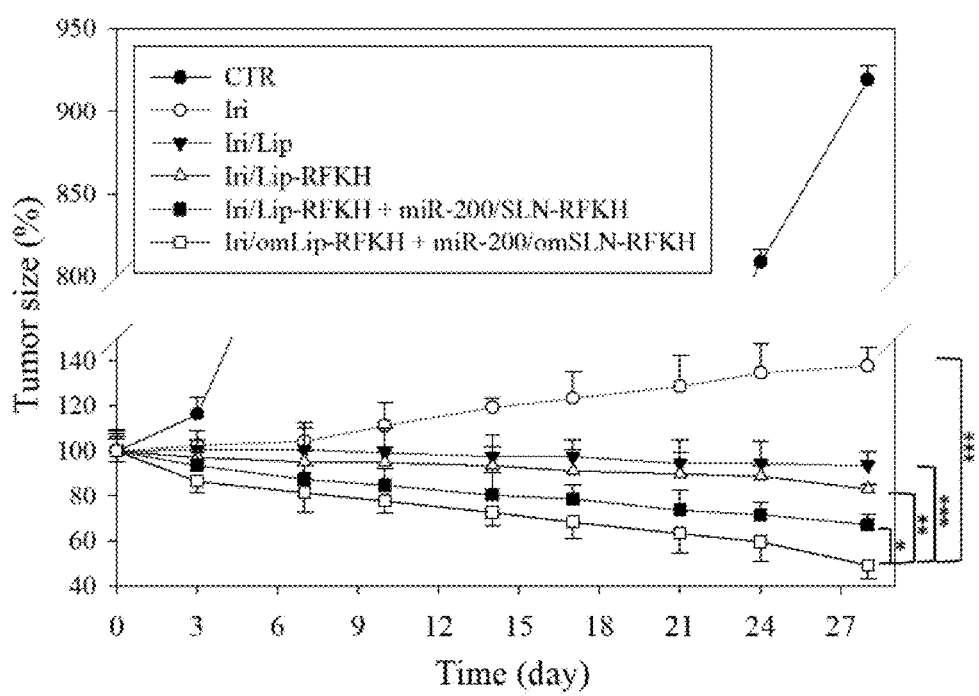
Figure 8D:
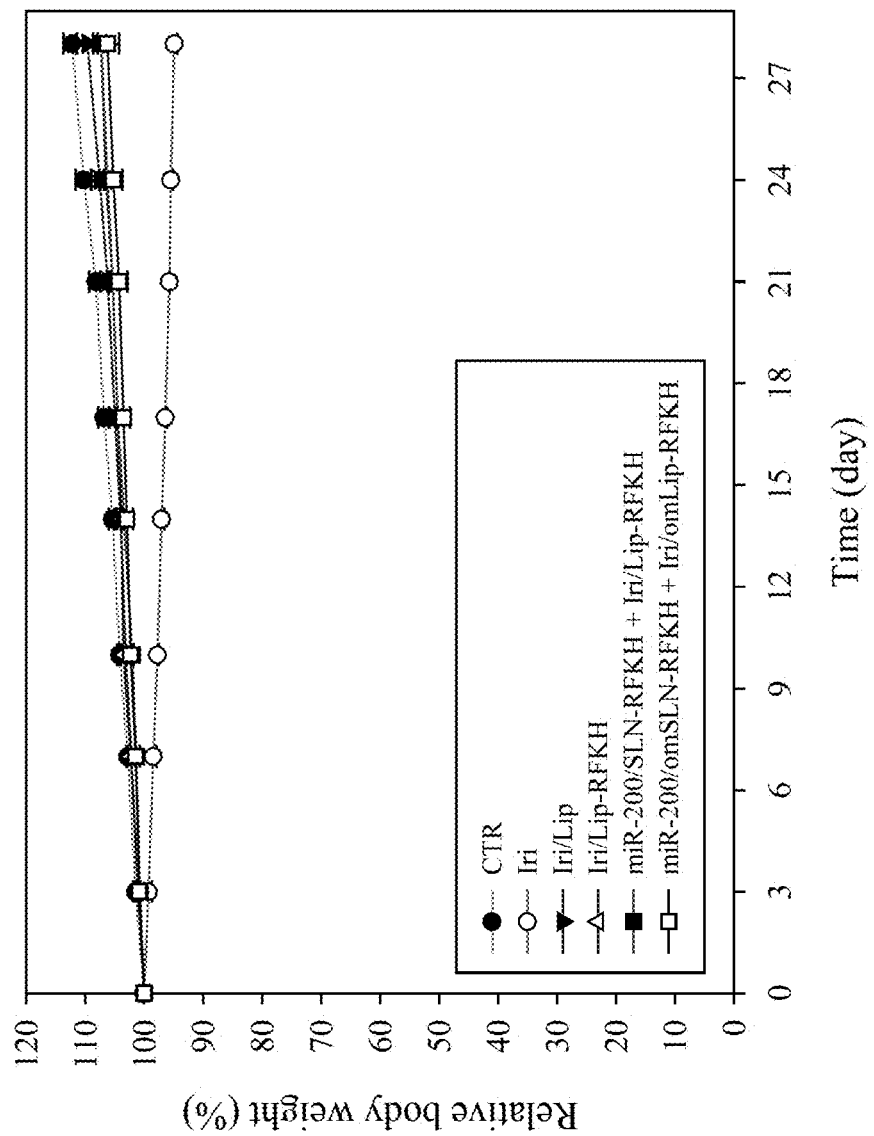

For safety assessment, CT26-bearing mice treated with Iri showed a continuous decrease in the body weight (FIG. 8D). All other groups displayed constant increases in body weight with minor individual differences (FIG. 8D).

Biochemical Tests and Hematoxylin and Eosin (H&E) Staining

Tumor-bearing mice were treated as described above. Blood samples (170 µl) were taken from the orbital sinus of mice 48 h after the final treatment. After harvesting and centrifugation for 15 min, liver, kidney and heart functions were assessed by detecting the serum levels of glutamate pyruvate transaminase (GPT), creatinine (CRE), and creatine kinase-MB (CK-MB) using corresponding activity assay kits (Fujifilm, Tokyo, Japan) and a clinical dry chemistry analyzer (Fuji Dri-Chem 7000V, Fujifilm Corp.). Additionally, the tumors and intestines were fixed in 4% paraformaldehyde overnight, embedded in paraffin, and cut into 5-µm-thick sections for H&E staining, and the histology of these samples was examined using an Olympus microscope.

TUNEL Assay

TUNEL assay was performed to assess in vivo apoptosis in CT26 tumor-bearing mice at 48 h after last treatment of different formulations.[42] In brief, the samples were frozen and fixed in 4% paraformaldehyde for 20 min. After washing with PBS for 10 min, the samples were immersed on ice for 2 min. After mixing with reaction dispersion (50 µL) according to the manufacture's manual (In Situ Cell Death Detection Kit, Roche, Germany), the section samples were stained with Hoechst in the nuclei for comparison and monitored using CLSM.

Statistical Analysis

Results are expressed as the mean±standard deviation (SD). Statistical significance was analyzed using Student's t-test to compare differences between two treatment groups. Statistical analysis was also conducted using one-way ANOVA and Dunnett's multiple comparison tests. Differences were considered to be statistically significant if the P-value was less than 0.05.

Figure 9A:
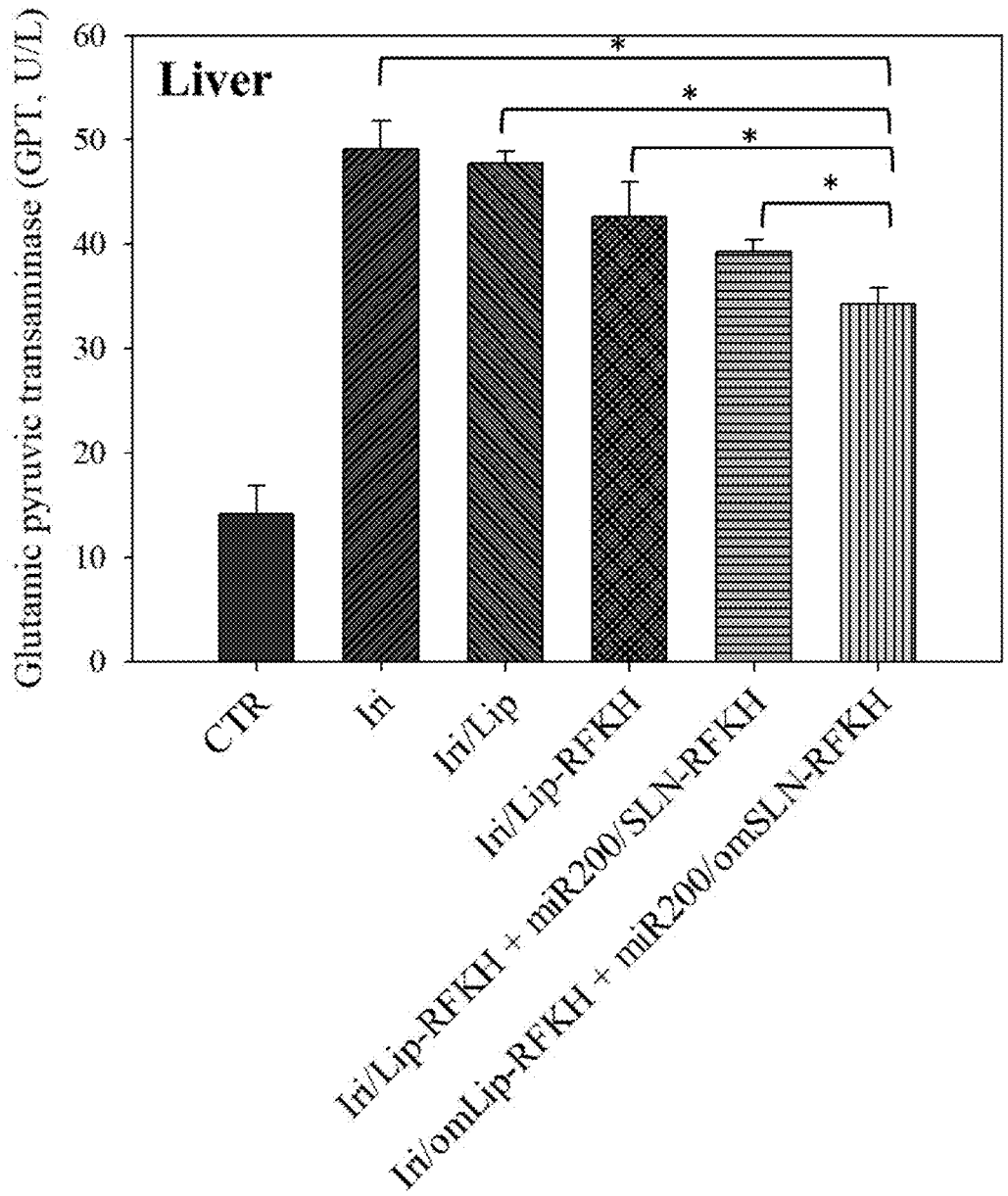
FIG. 9A shows serum levels of GPT at 48 h after last treatment of different formulations in colorectal cancer model.
Figure 9B:
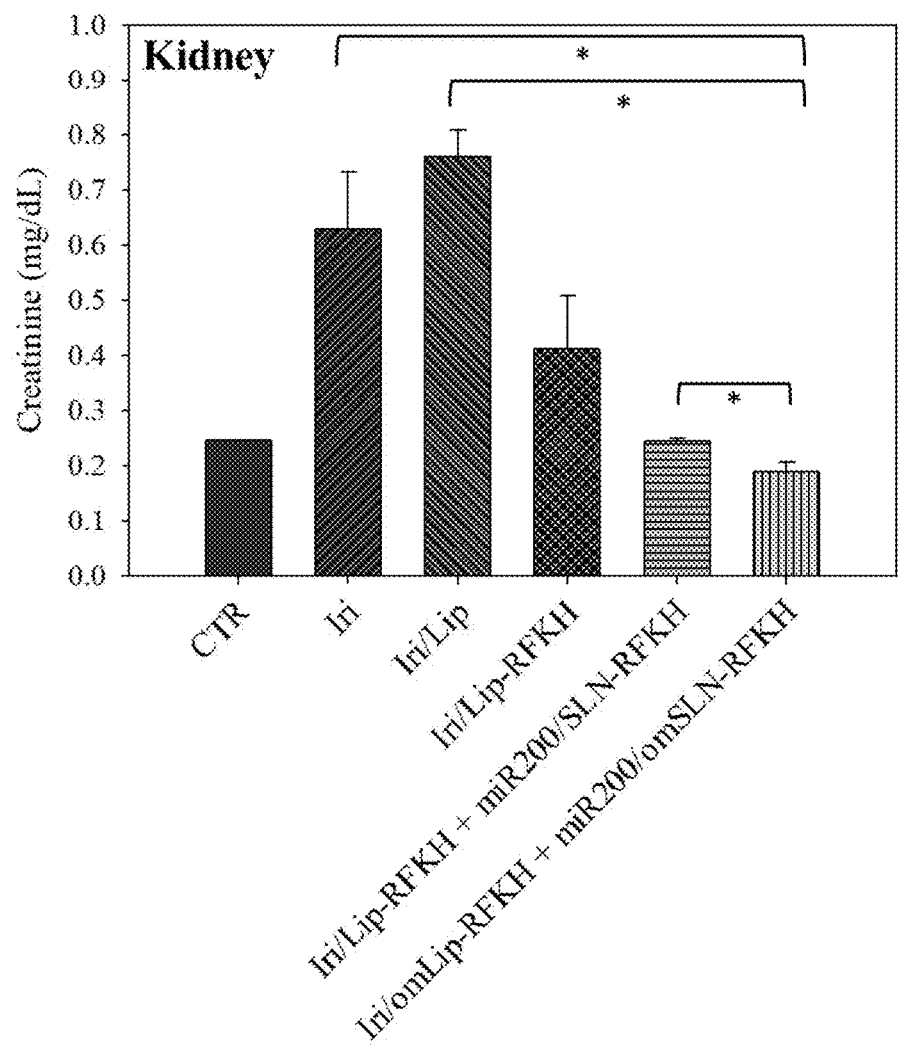
FIG. 9B shows CRE at 48 h after last treatment of different formulations in colorectal cancer model.
Figure 9C:
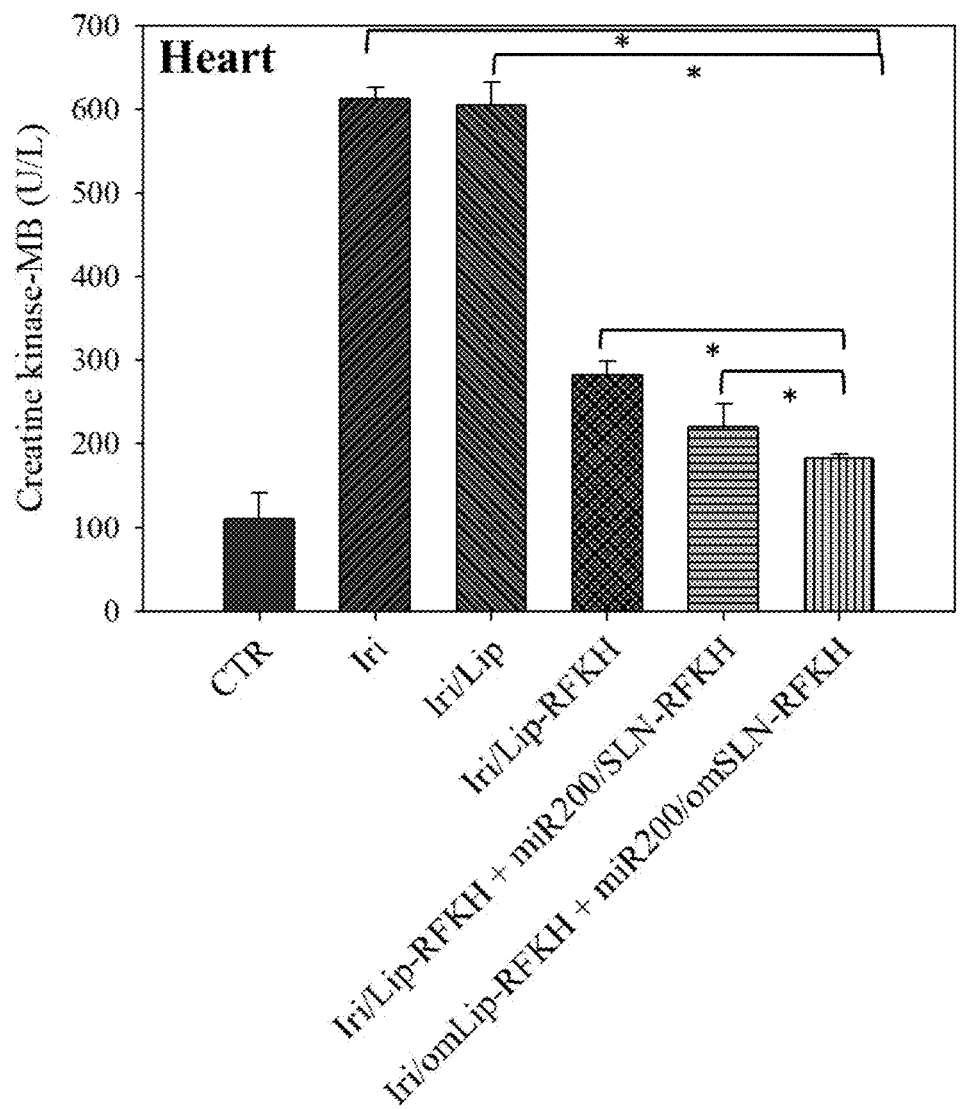
FIG. 9C shows CKMB at 48 h after last treatment of different formulations in colorectal cancer model.

Furthermore, serum GPT, CRE and CKMB levels were examined to evaluate liver, renal and heart functions, respectively (FIG. 9A-C). The results showed that serum GPT, CRE and CKMB levels were provoked after treatment with Iri or Iri/Lip (FIG. 9A-C), indicating substantial damage induced by Iri or Iri/Lip to the liver, kidney and heart.

Figure 6B:
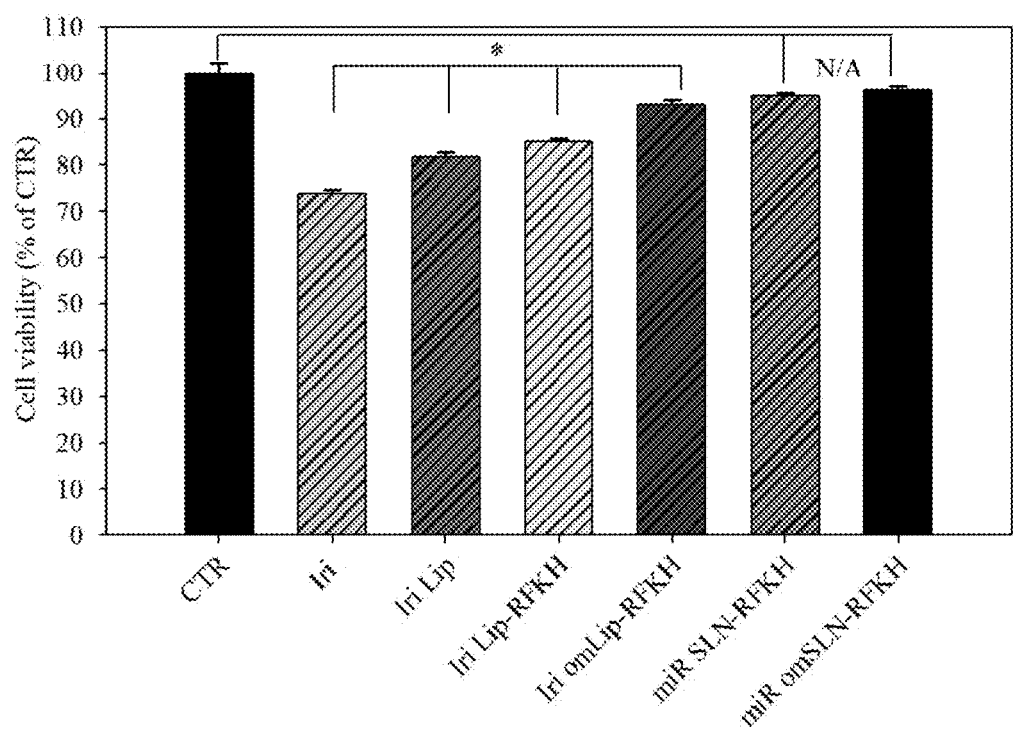
FIG. 6B shows cytotoxicity of various formulations on IEC-6. The cell viability was determined by sulforhodamine B assay. Cytotoxicity of different formulations on IEC-6 cells for 48 h. *P<0.05 compared to CTR. †P<0.05 compared to Iri/Lip. ‡P<0.05 compared to Iri/Lip-RFKH. NC: scrambled miRNA.
Figure 6C:
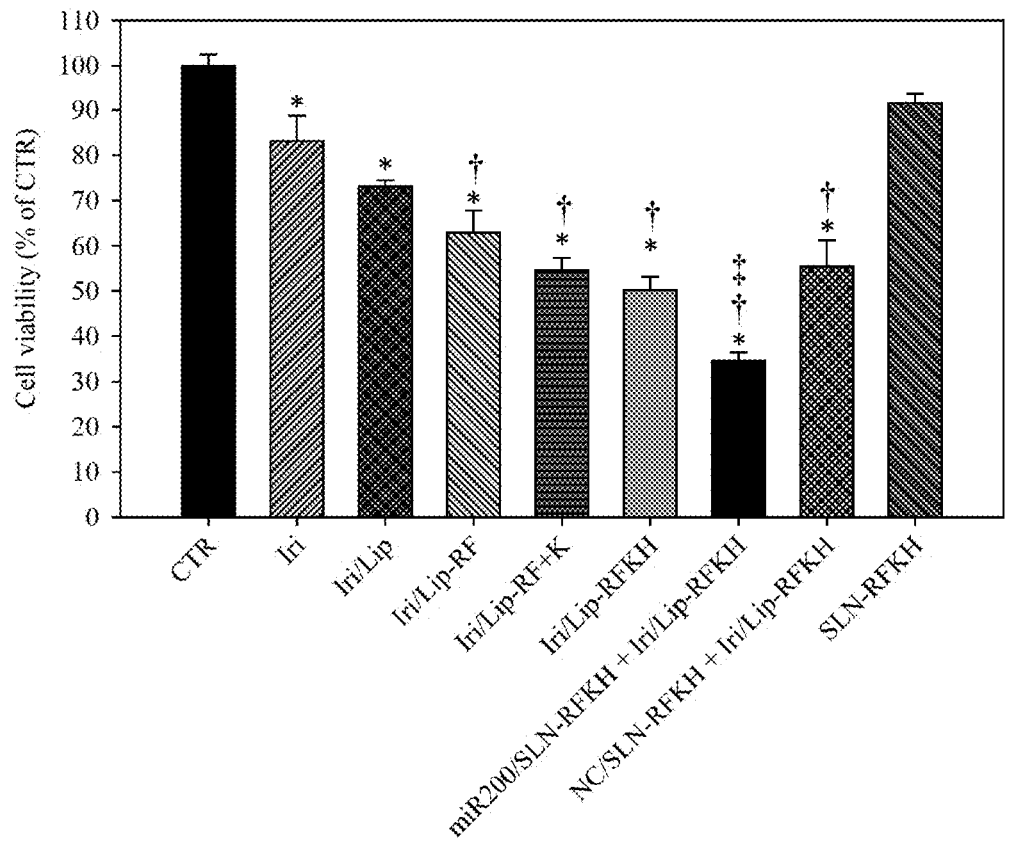
FIG. 6C shows cytotoxicity of various formulations on HCT116 cells. The cell viability was determined by sulforhodamine B assay. Cytotoxicity of different formulations on HCT116 cells for 48 h. *P<0.05 compared to CTR. †P<0.05 compared to Iri/Lip. ‡P<0.05 compared to Iri/Lip-RFKH. NC: scrambled miRNA.
Figure 9D:
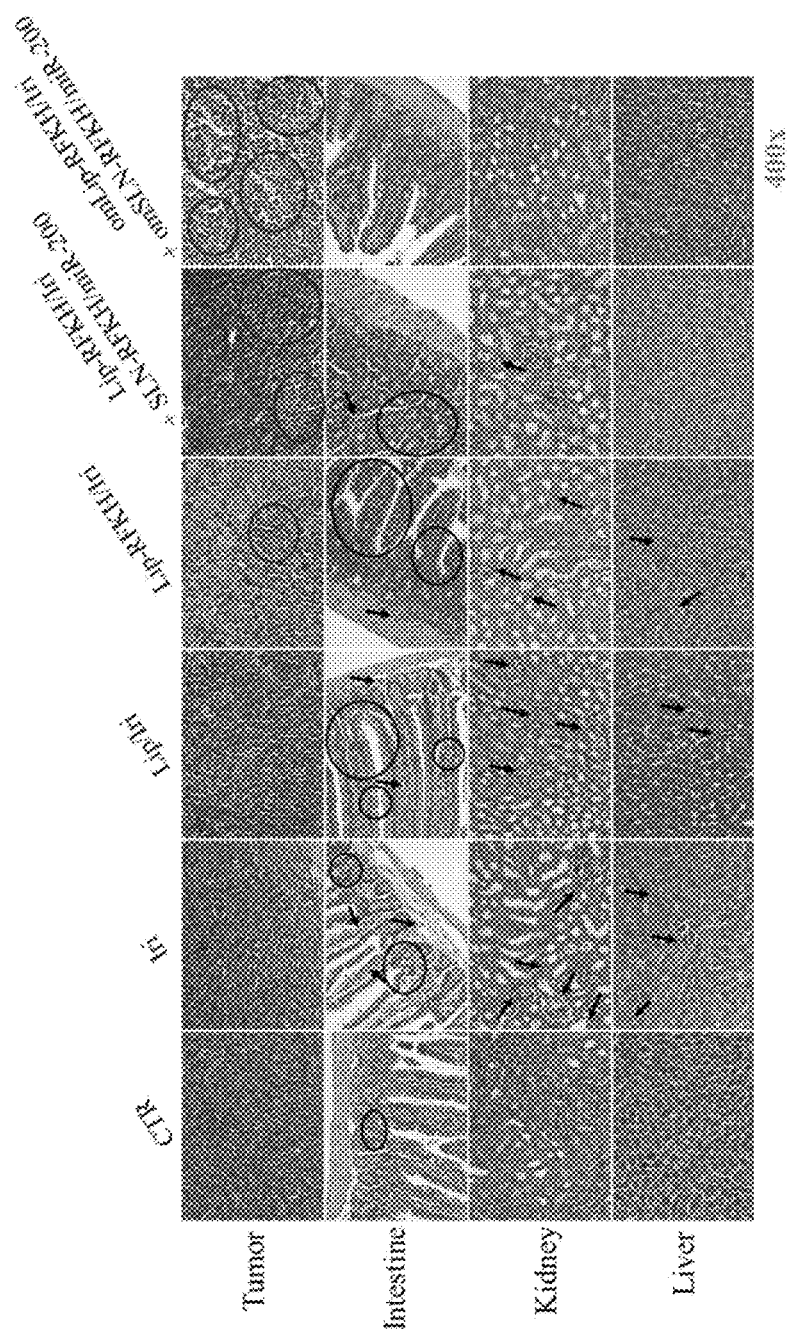
FIG. 9D shows photomicrographs of H&E staining of mouse tissues after last treatment of different formulations in colorectal cancer model.

Another problem solved in the current study was the toxicity associated with cationic gene delivery systems or chemotherapeutic agents, such as irinotecan (FIG. 6A-6B, 8D, 9A-9D, S3). Although our miR-200/SLN-RFKH exhibited a positive charge and Iri/Lip-RFKH demonstrated a negative charge (Table 1), these formulations showed low toxicity to both intestinal and blood cells (FIG. 6A-6B, S3AB). All the hemolysis percentage values of the prepared Lip and SLN formulations were lower than 10% (FIG. 6A, S3A), which follows the guideline suggesting that formulations must display hemolysis values of <10% to be considered nonhemolytic, while formulations with values >25% may have a risk of hemolysis. Furthermore, lower toxicity of Iri/omLip to IEC-6 cells compared with Iri, indicating that omLip might reduce irinotecan's GI side effects. Our in vivo results also suggested that omLip-RFKH and omSLN-RFKH were well tolerated and biocompatible (FIG. 9D). The shielding by pH-sensitive omPEG-lipid layer to release less cargos to normal cells might reduce the toxicity. The remarkable declines in vacuoles, interstitial hemorrhage, tissue degeneration and serum levels of GPT, CRE and CKMB suggest the mitigation of tissue injury and inflammation after the pH-responsive PEG coating (FIG. 9A-9D). Hence, the application of Iri/omLip-RFKH alone or in combination with miR-200/omSLN-RFKH may benefit from the diminished adverse events such as GI toxicity and thus may increase their clinical implications. However, the tumor cells exhibited the morphological features of pyknosis, demonstrating tumor necrosis and apoptosis after various treatments, especially in the group of Iri/Lip-RFKH+miR-200/SLN-RFKH (FIG. 9D, first panel). Tumor apoptosis was particularly noticeable for this combined treatment group, as exhibited in Figure S5).

Furthermore, the most profound reduction in tumor signal was observed in the miR-200/omSLN-RFKH+Iri/omLip-RFKH treatment group via IVIS and PET/CT images (FIG. 8A-8B). Moreover, the anticancer efficacy and evidence of tumor cell apoptosis and necrosis were also verified by tumor size measurement (FIG. 8C) and tumor HE staining (FIG. 9D, first panel) and TUNEL assay. The overall scheme for modulation of apoptosis signaling pathway by the combination of a cleavable PEG coating on peptide RFHK-modified Lip and SLN incorporating irinotecan and miR-200 in a colorectal cancer model is shown in FIG. 3.

Collectively, after combined treatment with Iri/Lip-RFKH+miR-200/SLN-RFKH, CRC cell growth was significantly reduced and the anticancer efficacy was remarkably enhanced in colon tumor-bearing mice. Apoptosis was the major mechanism involved in colon cancer cell death. Overall, successful delivery of miR-200 by omSLN-RFKH and irinotecan by omLip-RFKH modulated the β-catenin/MDR/apoptosis/EMT signaling pathways and suppressed the expression of Rac-1, KRAS, p-GSK-3β, β-catenin, cyclin D1, c-Myc, P-gp, MRPs, ZEB1, Slug, and Vimentin, thus effectively inhibiting tumor growth in colorectal cancer.

Figure 10:
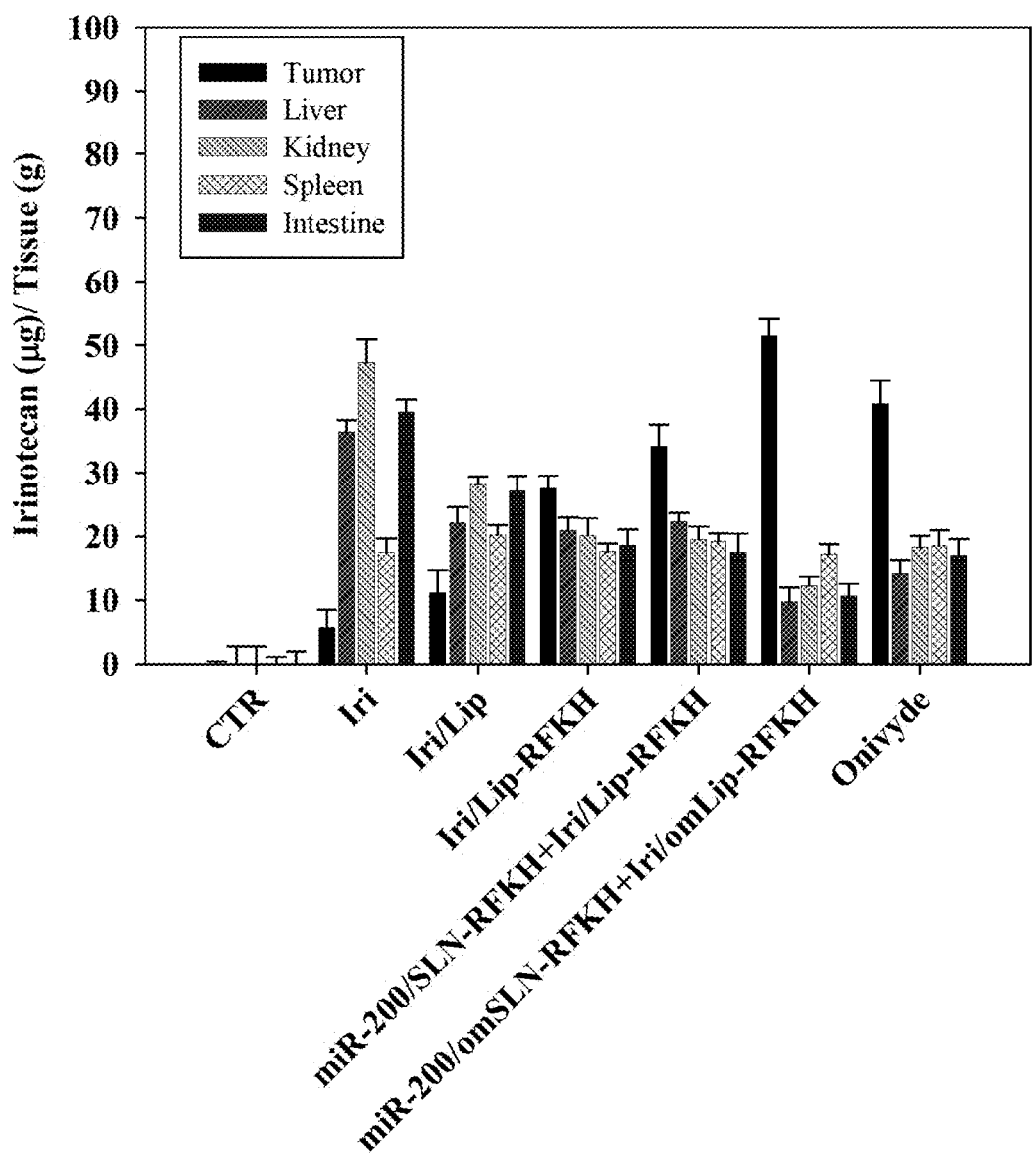
FIG. 10 shows biodistribution of different formulations in CT26/tk-luc-bearing mice. The biodistribution of irinotecan of different formulations in CT26-bearing mice was analyzed by UV spectrophotometer (*statistical significance at P<0.05; statistical significance at P<0.01; *statistical significance at P<0.001). The biodistribution of irinotecan of different formulations in CT26-bearing mice was analyzed by UV spectrophotometer. The result indicated that Iri without Lip encapsulation was distributed mainly in the liver, kidney, and intestines. However, Iri formulated in Iri/Lip-RFKH+miR-200/SLN-RFKH, Iri/omLip-RFKH+miR-200/omSLN-RFKH, and Onivyde was accumulated predominantly in the tumor tissue, especially for the pH-sensitive om-treatment group. Our finding further suggests that superior tumor accumulation of this tumor microenvironment-shiftable combined treatment of Iri and miR-200, mostly due to its pH-responsive and tumor-targeting design.

Example 8. Biodistribution of Different Formulations in CT26/Tk-Luc-Bearing Mice The biodistribution of irinotecan of different formulations in CT26-bearing mice was analyzed by UV spectrophotometer (*statistical significance at P<0.05; statistical significance at P<0.01; *statistical significance at P<0.001). As shown in FIG. 10, the biodistribution of irinotecan of different formulations in CT26-bearing mice was analyzed by UV spectrophotometer. The result indicated that Iri without Lip encapsulation was distributed mainly in the liver, kidney, and intestines. However, Iri formulated in Iri/Lip-RFKH+miR-200/SLN-RFKH, Iri/omLip-RFKH+miR-200/omSLN-RFKH, and Onivyde was accumulated predominantly in the tumor tissue, especially for the pH-sensitive om-treatment group. Our finding further suggests that superior tumor accumulation of this tumor microenvironment-shiftable combined treatment of Iri and miR-200, mostly due to its pH-responsive and tumor-targeting design.

Figure 11:
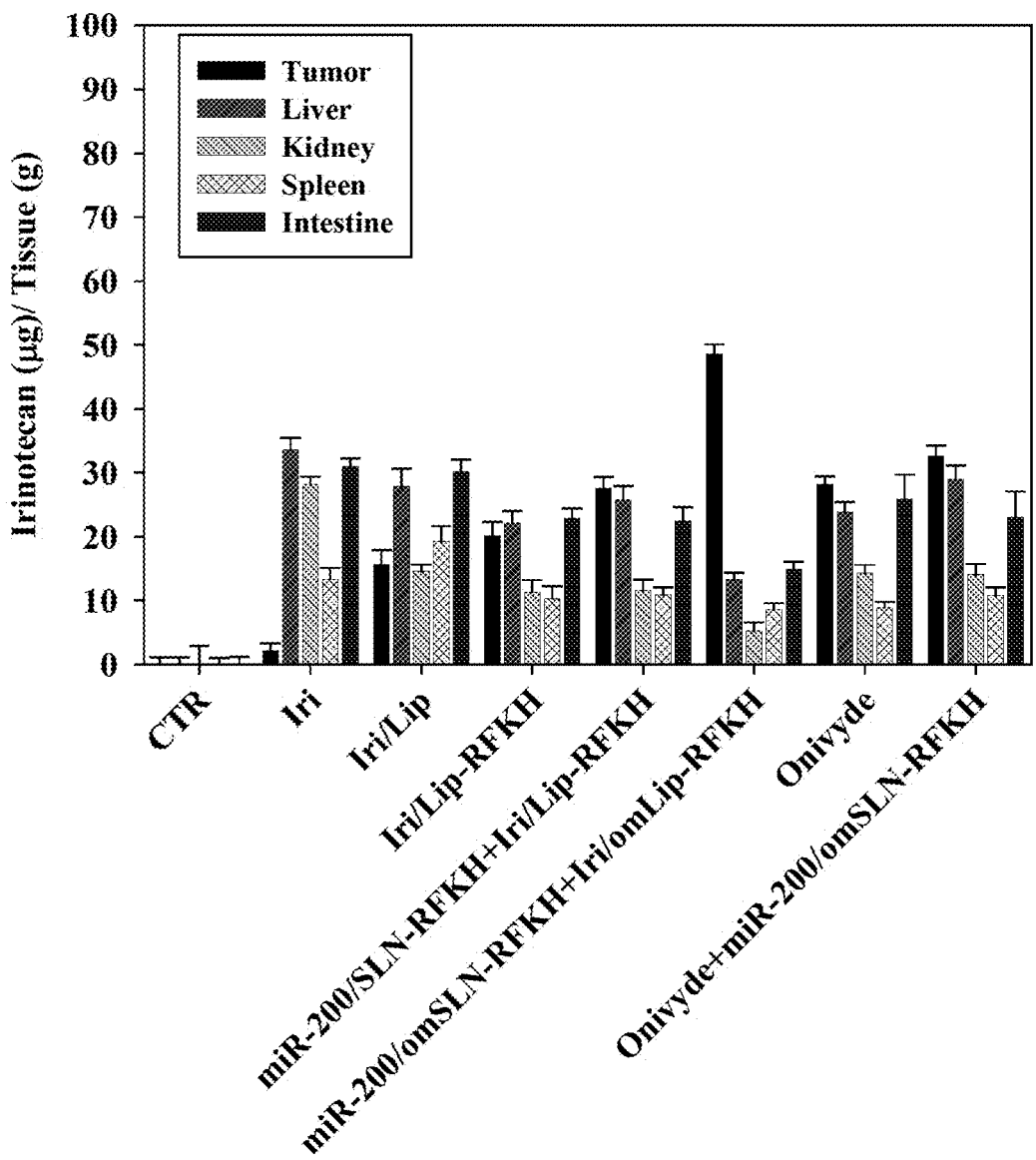
FIG. 11 shows biodistribution study of irinotecan of different formulations in SAS-luc-bearing nude mice. The biodistribution of irinotecan of different formulations in SAS-bearing mice was analyzed with UV spectrophotometer. (*statistical significance at P<0.05; statistical significance at P<0.01; *statistical significance at P<0.001). The biodistribution of irinotecan of different formulations in SAS-bearing mice was detected and the result demonstrated that Iri solution was distributed majorly in the liver, kidney, and intestines. Nevertheless, Iri incorporated in Iri/Lip-RFKH+miR-200/SLN-RFKH, Iri/omLip-RFKH+miR-200/omSLN-RFKH, and Onivyde was distributed primarily in the tumor tissue, particularly for the pH-sensitive omLip and omSLN group. Our finding further indicates that the excellent tumor accumulation of this tumor-detachable biomaterial to prepare nanoparticles for delivering Iri and miR-200 specifically to the HNC tumor site.

Example 9. Biodistribution Study of Irinotecan of Different Formulations on SAS-Luc-Bearing Nude Mice The biodistribution of irinotecan of different formulations in SAS-bearing mice was analyzed with UV spectrophotometer. (*statistical significance at $P<0.05$; statistical significance at $P<0.01$; *statistical significance at $P<0.001$). As shown in FIG. 11, the biodistribution of irinotecan of different formulations in SAS-bearing mice was detected and the result demonstrated that Iri solution was distributed majorly in the liver, kidney, and intestines. Nevertheless, Iri incorporated in Iri/Lip-RFKH+miR-200/SLN-RFKH, Iri/omLip-RFKH+miR-200/omSLN-RFKH, and Onivyde was distributed primarily in the tumor tissue, particularly for the pH-sensitive om-PEG group (FIG. 11). Our finding further indicates that the excellent tumor accumulation of this tumor-detachable biomaterial to prepare nanoparticles for delivering Iri and miR-200 specifically to the HNC tumor site.

What is claimed is:

1. A pH-sensitive lipid nanoparticle, comprising:
 a surface of the lipid nanoparticle; and
 a targeting agent inside the lipid nanoparticle,
 wherein the surface comprising:
 an imine-omPEG, the imine is a pH-sensitive linker;
 a PEG-RF peptide, wherein the RF peptide is a potent cell-penetrating peptide (CPP) and has an amino acid sequence of SEQ ID NO:1;
 a PEG-K peptide, wherein the K peptide is a mitochondria-targeting peptide) and has an amino acid sequence of SEQ ID NO:2; and
 a PEG-H peptide, wherein the H peptide is a cancer specific binding peptide, a nerve/glial antigen 2 (NG2) proteoglycan binding peptide, and has an amino acid sequence of SEQ ID NO:3,
 wherein the lipid nanoparticle is composed of a lipid, a cationic lipid, a surfactant, or a phospholipid.

2. The lipid nanoparticle of claim 1, wherein the lipid is a L-α-phosphatidylcholine (PC), glycerol monostearate (monostearin), glycerol monopalmitate or glycerol monooleate.

3. The lipid nanoparticle of claim 1, wherein the cationic lipid is DOTAP, DOTMA, SAINT 2, MC3, or KC2.

4. The lipid nanoparticle of claim 1, wherein the phospholipid is DSPE, DPPE, or DOPE.

5. The lipid nanoparticle of claim 1, wherein the surfactant is Poloxamers (Pluronics), Tweens, Spans, Brij, Myrj, cyclodextrin derivative, or chitosan derivative.

6. The lipid nanoparticle of claim 1, wherein the targeting agent is selected from the group consisting of a microRNA and a drug.

7. The lipid nanoparticle of claim 6, wherein the microRNA is selected from the group consisting of hsa-miR-21 inhibitor mimics for has-miR-122-5p, hsa-miR-125b-5p, has-miR-136-5p, has-miR-139-5p, has-miR-200c-3p and has-miR-320a.

8. The lipid nanoparticle of claim 6, wherein the drug is selected from the group consisting of irinotecan, oxaliplatin, epirubicin, doxorubicin, afatinib, and docetaxel.

9. The lipid nanoparticle of claim 1, wherein the lipid nanoparticle can be accumulated in a cancer cell in pH 5-7 environment or tumor microenvironment.

10. The lipid nanoparticle of claim 1, wherein the cancer is colorectal cancer, head cancer and neck cancer, or pancreatic cancer.

11. A pharmaceutical composition comprising:
 an effective amount of the pH-sensitive lipid nanoparticle as claim 1, comprising:
 a microRNA-loaded pH-sensitive lipid nanoparticle, wherein the lipid is a mixture of a monoglyceride, the cationic lipid and the surfactant, and the targeting agent is a microRNA; and
 a drug-loaded pH-sensitive lipid nanoparticle, wherein the lipid is a lipid bilayer composed of the phospholipid and the targeting agent is an anticancer drug.

12. The pharmaceutical composition of claim 11, wherein the microRNA is selected from the group consisting of hsa-miR-21 inhibitor, mimics for has-miR-122-5p, hsa-miR-125b-5p, has-miR-136-5p, has-miR-139-5p, has-miR-200c-3p and has-miR-320a.

13. The pharmaceutical composition of claim 11, wherein the anticancer drug is selected from the group consisting of the irinotecan, oxaliplatin, epirubicin, doxorubicin, afatinib, and docetaxel.

14. A method for treating cancer in a subject, comprising:
 administering to said subject an effective amount of the pH-sensitive lipid nanoparticle of claim 1, wherein the pH-sensitive lipid nanoparticle comprises:
 a microRNA-loaded pH-responsive lipid nanoparticle, wherein the lipid is a mixture of a monoglyceride, the cationic lipid, and the surfactant, and the targeting agent is a microRNA; and
 a drug-loaded pH-responsive lipid nanoparticle, wherein the lipid is a lipid bilayer composed of a phospholipid, and the targeting agent is an anticancer drug,
 wherein the cancer is colorectal cancer or head and neck cancer, the anticancer drug corresponding to the cancer is irinotecan, the microRNA corresponding to the cancer is miR-200.

* * * * *

SEQUENCE LISTING

```
<160> NUMBER OF SEQ ID NOS: 3

<210> SEQ ID NO 1
<211> LENGTH: 17
<212> TYPE: PRT
<213> ORGANISM: Artificial Sequence
<220> FEATURE:
<223> OTHER INFORMATION: RF peptide synthesized from the laboratory

<400> SEQUENCE: 1

Gly Leu Lys Lys Leu Ala Arg Leu Phe His Lys Leu Leu Lys Leu Gly
1               5                   10                  15

Cys

<210> SEQ ID NO 2
<211> LENGTH: 8
<212> TYPE: PRT
<213> ORGANISM: Artificial Sequence
<220> FEATURE:
<223> OTHER INFORMATION: K peptide synthesized from the laboratory

<400> SEQUENCE: 2

Cys Lys Leu Ala Lys Leu Ala Lys
1               5

<210> SEQ ID NO 3
<211> LENGTH: 11
<212> TYPE: PRT
<213> ORGANISM: Artificial Sequence
<220> FEATURE:
<223> OTHER INFORMATION: H peptide synthesized from the laboratory

<400> SEQUENCE: 3

Cys Thr Ala Ala Ser Gly Val Arg Ser Met His
1               5                   10
```